(12) United States Patent
Farrell

(10) Patent No.: US 8,459,987 B2
(45) Date of Patent: Jun. 11, 2013

(54) ORTHODONTIC APPLIANCE

(76) Inventor: Christopher John Farrell, Helensvale (AU)

( * ) Notice: Subject to any disclaimer, the term of this patent is extended or adjusted under 35 U.S.C. 154(b) by 0 days.

(21) Appl. No.: 13/362,584

(22) Filed: Jan. 31, 2012

(65) Prior Publication Data

US 2012/0196243 A1    Aug. 2, 2012

Related U.S. Application Data

(63) Continuation of application No. 12/657,488, filed on Jan. 20, 2010, now Pat. No. 8,105,079, which is a continuation-in-part of application No. 11/787,661, filed on Apr. 16, 2007, now abandoned, which is a continuation-in-part of application No. PCT/AU2005/001598, filed on Oct. 14, 2005.

(30) Foreign Application Priority Data

Oct. 14, 2004 (AU) .............................. 2004905924

(51) Int. Cl.
*A61C 5/14* (2006.01)

(52) U.S. Cl.
USPC ............................................................ 433/6

(58) Field of Classification Search
USPC ........................................ 433/6; 128/861, 862
See application file for complete search history.

(56) References Cited

U.S. PATENT DOCUMENTS

| | | | | |
|---|---|---|---|---|
| 5,511,562 | A * | 4/1996 | Hancock | 128/859 |
| 8,105,079 | B2 * | 1/2012 | Farrell | 433/6 |
| 2004/0154626 | A1 * | 8/2004 | Washburn et al. | 128/861 |

* cited by examiner

*Primary Examiner* — Ralph Lewis
(74) *Attorney, Agent, or Firm* — Berenato & White, LLC

(57) ABSTRACT

An orthodontic appliance 1 for promoting development of a dental arch form in a patient. The appliance 1 includes an arch-shaped base member 2 that is made of a resiliently flexible material, and a teeth engaging member 5 that encloses at least part of the base member 2. The teeth engaging member 5 defines upper and/or lower dental arch receiving channels 46, 47 and is made of a resiliently flexible material that is deformable. The appliance 1 has a resting form in which the resilient materials of the base member 2 and the teeth engaging member 5 are in their resting condition. The appliance 1 can be flexed or deformed out of the resting form to fit the underdeveloped dental arch form into the dental arch receiving channel 46, 47. When deformed the appliance 1 exerts a return force that urges the underdeveloped dental arch to expand.

20 Claims, 13 Drawing Sheets

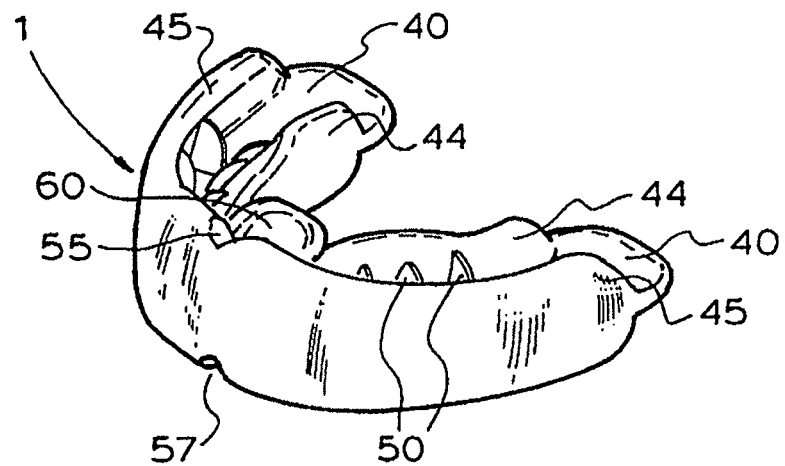
Fig_13.
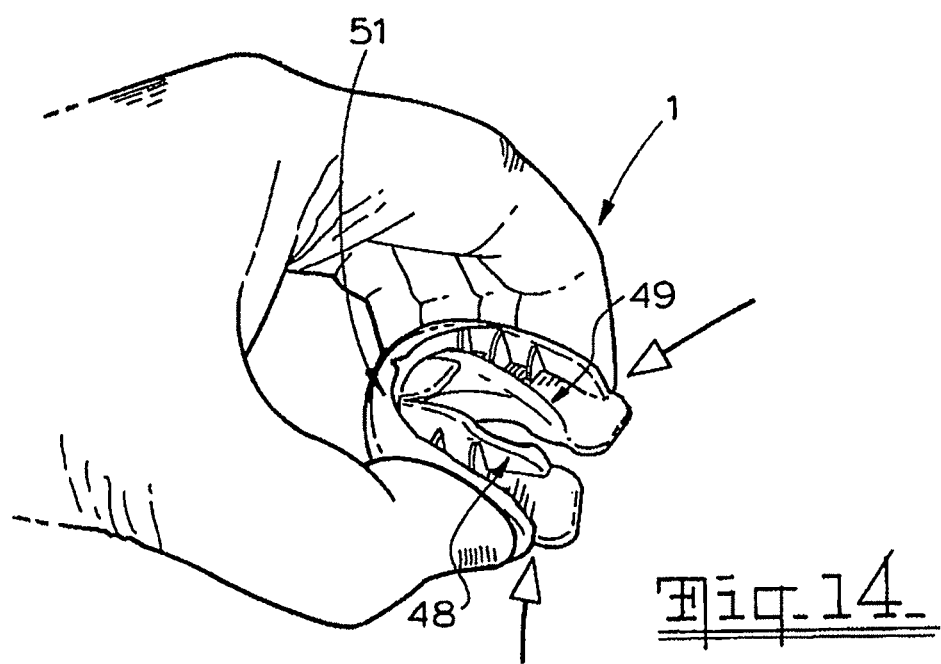
Fig_14.

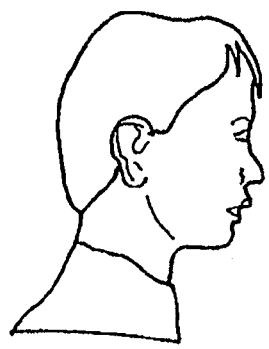
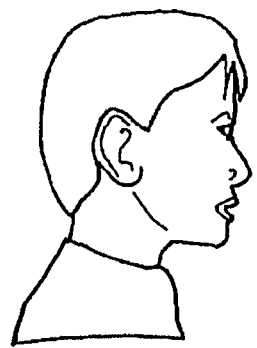
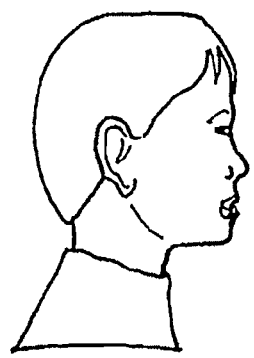
Fig.19.

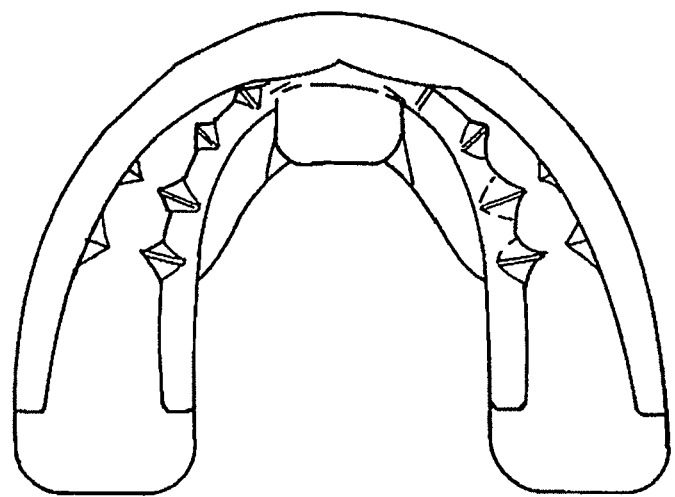
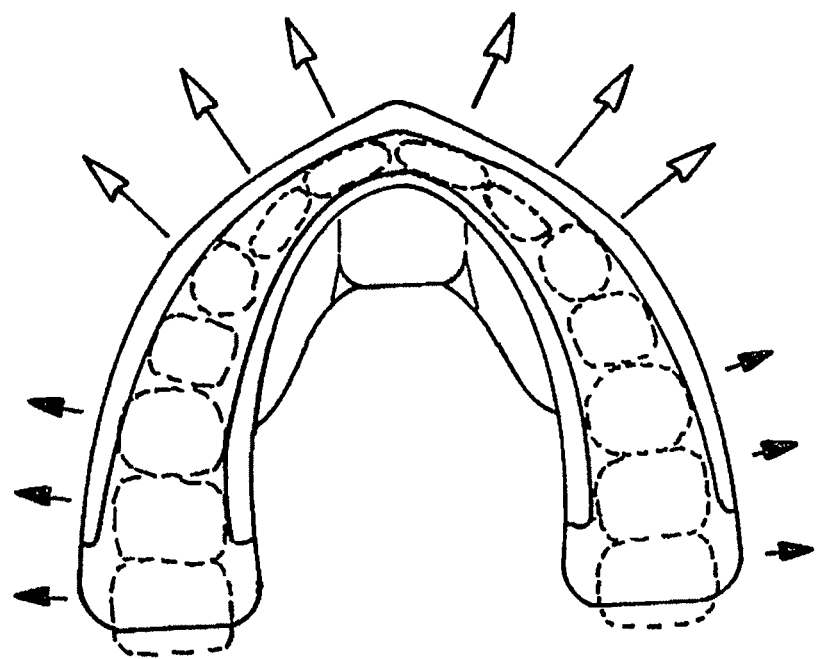
Fig. 20.

ORTHODONTIC APPLIANCE

This application is a continuation of U.S. application Ser. No. 12/657,488, filed Jan. 20, 2010 now U.S. Pat. No. 8,105,079, which was a continuation-in-part of U.S. application Ser. No. 11/787,661, filed 16 Apr. 2007, now abandoned, which was a continuation-in-part of PCT/AU05/01598, filed on 14 Oct. 2005, which designated the United States, now lapsed, which claimed priority to AU 2004 905924 filed on 14 Oct. 2004.

FIELD OF THE INVENTION

This invention relates to an orthodontic appliance for use in orthodontic treatment for developing an underdeveloped arch into a developed arch form.

This invention relates particularly but not exclusively to an orthodontic appliance for use in treating a Class 2 malocclusion by promoting expansion of an underdeveloped upper dental arch. It will therefore be convenient to hereinafter describe the invention with reference to this example application. However it is to be clearly understood that the invention is capable of broader application. For example it can find application in orthodontic treatments other than those seeking to expand the patient's arch form. It can also find application in the treatment of malocclusions other than class 2 malocclusions.

DEFINITIONS

In this specification the term "engaging" shall bear a broad meaning and shall not be limited to a retaining or latching engagement.

In this specification the term "flange" shall bear a broad meaning and shall not be limited to a radially extending wall at the end of a cylindrical section. It shall be understood to include a wall or wall like formation that extends transversely away from another surface, e.g. a web surface.

In this specification the term "correct dental occlusion" shall bear a broad meaning and shall refer to an occlusion where the dentition of the upper and the lower arches come together in a correct positioning relative to each other along the length of the arch.

In this specification the term "dental arch and associated dental structures" shall bear a broad meaning and shall include the bone of the dental arch and the surrounding bony gum tissues and soft gum tissues. It shall also be understood to include the dentition on the arch.

BACKGROUND TO THE INVENTION

One type of orthodontic appliance that is known is a custom made plate appliance that is made in a dental laboratory and is moulded from bite impressions of the dental arches and associated dental structures of that particular patient. The bite impressions are used to make laboratory models of that particular patient's arches and associated dental structures. These models are then used to mould a customised appliance including a plate that is shaped and configured to be complementary to that particular user's dental arch and thereby closely fit that user's dental arch and arch structures.

A limitation of plate appliances is that the cost of producing them is high because they are individually made for each patient in a dental laboratory based on a dental model of the patient and a bite impression of the patient.

Orthodontic systems using fixed appliances that are commonly called orthodontic braces are also used for orthodontic treatment. Orthodontic braces comprise a plurality of brackets each of which is mounted over an individual tooth and bonded thereto so that it is permanently mounted on the tooth. The brackets are linked together by means of a wire that passes through wire apertures formed in each of the brackets. The wire applies a force to the brackets that can then reposition and align the teeth on the dental arch.

In particular these fixed appliances can be used to bring the anterior teeth on the upper and lower arches in the correct relative position to each other. The wire can progressively be drawn in to retract the incisor teeth on the anterior region of the upper dental arch to "close" an "open" bite.

These fixed appliances using brackets focus on moving teeth on a dental arch, particularly to align the teeth. For example they can be used to retract protruding teeth, in particular protruding incisors on the upper arch of a user, and they can also be used to advance retruded teeth.

The fixed appliances described above have their drawbacks. Firstly Applicant's experience is that most orthodontic patients would choose not to wear braces if an alternative treatment was available. The brackets of the braces are generally unsightly and detract from the patient's looks while the braces are being worn, e.g. for the direction of the treatment. Secondly the braces can be uncomfortable to wear and can cause trauma, such as cuts and bruises to the intraoral soft tissues of a user. The soft buccal mucosa is particularly susceptible to injury from projections on the buccal surface of the brackets.

Thirdly the brackets and wire are permanently attached to the dentition and thus cannot be temporarily removed by a patient in the way that a removable appliance can be removed. If the braces are particularly uncomfortable at any point in time to a user they cannot be temporarily removed to afford the patient some respite from the discomfort.

Fourthly another problem that has plagued the use of braces is patient relapse. By this is meant that the teeth tend to move back to their original positions once the brackets are removed. The braces are permanent appliances so that when they are removed they cease to have any influence on teeth positioning. They cannot be used on an intermittent basis to provide a retaining function after the braces have been removed in the way that a removable appliance can be used. The braces do not offer a realistic or practical option as a retainer appliance once its use as an active appliance to achieve teeth repositioning is completed.

Aside from the traditional orthodontic treatments described above, in more recent times some treatments have focused on encouraging and promoting improved myofunctional habits as a way of developing an intraoral environment that is less predisposed to the development of severe class 2 and class 3 malocclusions. For example some orthodontic practitioners have recognised that poor oral habits such as tongue thrusting, incorrect swallowing, and mouth breathing create the conditions in which a malocclusion is likely to develop in a growing child.

The applicant has developed an arch shaped appliance having a front region and two arm regions to train a patient's or user's myofunctional habits so that the environment in which arch development and teeth positioning takes place is improved. In particular the appliance can train a patient to position certain key intraoral structures such as the tongue in the correct position and thereby resist the development of malocclusions that are caused by poor oral habits. One such feature is a tongue tab that assists in positioning the tongue at the correct height and to reduce tongue thrusting. The appliance also correctly positions the lower jaw or mandible of the patient relative to the upper jaw or maxillae. The appliance also encourages the patient to maintain their lips in a closed position and not to breathe through their mouth.

These appliances are integrally formed of a soft and resilient material such as PVC or silicon rubber. The soft and resilient material enables the appliance to be comfortably worn when it bears against the dental arch and arch structures such as the teeth and gums of a patient.

As the material from which the appliance is formed is soft and flexible it is easy to deform the appliance to move the arm regions of the appliance towards and away from each other and also to bend and twist the appliance. The resilience of the material will apply a return force tending to return the appliance to its original shape when it is distorted out of its original shape.

In a case where the appliance is deformed to enable it to be fitted onto the dental arch of a patient, the resilient nature of the appliance material may cause the appliance to apply some force to the arch of a patient when it is deformed. However because the appliance material is soft and flexible it does not exert a resilient force that is strong enough to significantly develop the bone structure of the dental arch of the user. In addition such an appliance does not make a significant contribution to alignment of the dentition on the associated arch. The primary orthodontic influence conferred by the appliance is to train the patient to adopt improved myofunctional habits. These improved myofunctional habits in turn encourage the patient's dental arch to develop in a way that leads to better dental occlusion over a period of time. The development of the arch form in turn provides an environment in which alignment of the dentition can be sought using other orthodontic contrivances and techniques.

It would be advantageous if an orthodontic appliance could be devised that directed a force onto the dental arch of a patient that was capable of developing the arch form of a user. It would further be advantageous if the orthodontic appliance was capable of achieving this arch development within a reasonable treatment time.

It would be further advantageous if an orthodontic appliance could be devised that was able to positively influence dental alignment of a patient's teeth along the dental arch as well as to develop the arch form.

It would be further advantageous if such an orthodontic appliance was removable so that it could be inserted into a patient's mouth, and also be removed from the patient's mouth during the course of treatment.

It would be advantageous if an orthodontic appliance could be devised that could be manufactured in a number of sizes in a moulding operation and these sizes could then be fitted to a significant cross-section of the population. This would create the potential to manufacture the appliance on a commercial scale.

SUMMARY OF THE INVENTION

According to one aspect of the invention there is provided an orthodontic appliance for promoting development of a dental arch form in a patient who has an underdeveloped dental arch, the appliance including:
- an arch-shaped base member that is made of a resiliently flexible material; and
- a teeth engaging member that encloses at least part of the base member and that defines at least one of upper and lower dental arch receiving channels, the teeth engaging member being made of a resiliently flexible material that is softer and/or flexible than the resiliently flexible material of the base member and that is deformable, wherein the appliance has a resting form in which the resilient materials of the base member and the teeth engaging member are in their resting condition, and wherein the appliance can be flexed or deformed out of the resting form to fit the underdeveloped dental arch form into the dental arch receiving channel, and when deformed the appliance exerts a return force that is directed to returning it to its resting form which in use urges the underdeveloped dental arch to expand into a developed dental arch form.

The appliance may have a resting form in which the dental arch receiving channel has a shape corresponding to the developed dental arch form that is sought to be achieved in the patient by using the appliance. The dental arch receiving channel may have a caternary shape corresponding to an arch form representing a correct dental occlusion when the appliance is in the resting form.

The appliance may have a flexibility that permits the appliance to be manually flexed or deformed out of the resting form to fit the underdeveloped dental arch into the dental arch receiving channel.

The appliance may include a front region that merges with two opposing arm regions that project away from either side of the front region, and the front region of the appliance may be less flexible than the arm regions and a flexure may be formed at either side of the front region when the arm regions are deflected towards each other.

The material of the base member and the material of the teeth engaging member may be selected so that they flex in unison with each other when they are deformed out of their resting conditions, and also so that the base member and the teeth engaging member resist delamination from each other when they are flexed out of their resting conditions.

The teeth engaging member may include an arch-shaped web that defines upper and lower occlusal bite surfaces, and the teeth engaging member may have inner and outer flanges that project transversely away from at least one of the upper and lower surfaces of the web, so that each dental arch receiving channel is defined between the web and the inner and outer flanges.

The web may have a front region and two free ends, and the web may decrease in transverse width in a direction from the free ends towards the front region so as to correspond with the decrease in width of the occlusal surfaces of a dental arch in a direction from a molar region towards an incisor region, so that the inner and outer flanges of the teeth engaging member may bear against the dental arch and arch structures, when the appliance is fitted.

The inner and outer flanges may project away from both the upper and lower surfaces of the web defining both upper and lower dental arch receiving channels within which respectively the upper and lower dental arches of a patient can be received.

The teeth engaging member may substantially fully enclose the base member. In particular the teeth engaging member may fully encase the entire base member outer surface.

The teeth engaging member may be made from a resiliently elastic material and the resilient elastic material of the teeth engaging member may be selected so that it is softer than intra-oral soft tissue, so as to form a soft cushioning material for bearing against the dental arch and dental structures of a patient.

The teeth engaging member may be made of a polymeric material that is silicone rubber, e.g. a medical grade silicone. The silicone material cushions the appliance against the dental arch and associated dental structures including teeth, gums and other intra-oral tissues of a user. Instead the polymeric material of the teeth engaging member may be made of a polyvinyl chloride (PVC).

The base member may be in the form of a generally arch shaped open frame structure and may define a front region and two arm regions each extending to a free end.

The open frame structure may include a curved outer frame member and a curved inner frame member that are, spaced apart from each other, and a plurality of spaced apart transverse frame members extending between the outer and inner frame members.

The outer frame member may be generally arch shaped and the inner frame member may be generally arch shaped so that the transverse spacing between the inner and outer frame members decreases from their free ends in a direction towards the front region of the appliance, so that an outline shape of the base member corresponds substantially with that of the web when viewed in plan view.

The base member may include a first pair of transverse frame members including one transverse frame member towards one side edge of the front region of the appliance and a further transverse frame member towards the other side edge of the front region, the left and right transverse frame members being positioned so that they align respectively with the left and right outer incisors of a patient when the appliance is fitted.

The one and further transverse frame members of the first pair may have a width of 1 to 4 mm, e.g. 2 to 3 mm.

The base member may include a front transverse frame member intermediate the first pair of transverse frame members.

The front transverse frame member may have a width of 5 to 15 mm (when measured extending from one side edge to the other. For example the front transverse frame member may have a width of 8 to 12 mm.

The front transverse frame member may be positioned substantially centrally with respect to the base member. The front transverse frame member may have a centre point midway along its length that is aligned with a midline of the base member. The front transverse frame member may extend across at least part of the two central incisors of a patient when the appliance is fitted to a patient.

The base member may further include a second pair of transverse frame members towards the free ends of the base members. The second pair of transverse frame members may comprise a left rear transverse frame member towards one free end and a right rear transverse frame member towards the other free end. In one form the left and right rear transverse frame members may form the free ends of the base member.

Each of the left and right rear transverse frame members may have a width of 2-10 mm, e.g. about 5 mm.

The base member may further include a third pair of transverse frame members positioned intermediate the first and second pairs of transverse frame members.

The third pair of transverse frame members may comprise a left transverse frame member positioned intermediate said transverse frame member of the first pair and the left rear transverse frame member, and a right transverse frame member positioned intermediate said right transverse frame member of the first pair and the right rear transverse frame member. The third pair of intermediate transverse frame members may be positioned adjacent to the first premolars on the dental arch when the appliance is fitted to the patient, which are the fourth teeth on the arch located in the first and second quadrants.

The third pair of intermediate transverse frame members may be positioned closer to the left and right rear transverse frame members than said left and right transverse frame members of the first pair on the front region of the base member.

Each pair of intermediate transverse frame members may be symmetrically arranged on each side of a midline of the base member, e.g. the arrangement of transverse frame members on the base member may be bilaterally symmetrical.

The base member may further include a teeth row repositioning formation projecting away from the curved outer frame member. The teeth row repositioning formation may comprise an outer flange that projects up above the curved outer frame member.

The outer flange may include a continuous wall on the central front region of the base member that extends across the upper incisor teeth of a patient in use. The central front region may extend up to a height of 2 to 10 mm above the transverse frame members, e.g. an upper surface of the adjacent or proximate transverse frame members.

The continuous wall may also extend along the left and right arm regions of the base member that are aligned with some of the molars of a user when the appliance is fitted to a patient. The left and right flange arm regions may extend up to a height of 2 to 6 mm above the transverse frame members, e.g. an upper surface of the adjacent or proximate transverse frame members.

The continuous wall may extend in a substantially uninterrupted fashion along the length of the base member and the height of the continuous wall may vary along the length of the wall.

The outer flange may be formed integrally with the open frame structure, e.g. in an injection moulding operation.

The base member may further include a further teeth row repositioning formation projecting away from the curved inner frame member.

The further teeth row repositioning formation may comprise an inner flange projecting up from the curved inner frame member above the height of the transverse frame members.

The inner flange on the curved inner frame member may extend a distance of about 1-3 mm, e.g. about 2 mm up from the transverse frame members, e.g. on the upper surface of the adjacent or proximate transverse frame members.

The inner flange may project up above the transverse frame members along at least the front region of the curved inner frame member. The inner flange may project up from the transverse frame members along the full length of the curved inner frame member. Further the inner flange may have substantially the same height along its full length.

The inner flange may also be formed integrally with the open frame structure, e.g. in an injection moulding operation.

In one form of the invention neither the outer flange on the curved outer frame member nor the inner flange on the curved inner frame member extends or depends downwardly below the plane of the open frame to any appreciable extent.

However it needs to be appreciated that an appliance with one or more downwardly depending flanges is contemplated to be within the scope of the invention. Applicant has found that with the base member materials that he has used, a satisfactory stiffness and strength can be obtained with outer and inner flanges that project up from the open frame but not down from the open frame. However if greater rigidity is required to be conferred by the base member for the appliance to perform its orthodontic function, then the inner and/or outer flanges could depend downwardly from the open frame as well as projecting upwardly.

In a further alternative the inner and outer flanges described above could also be provided projecting down from the plane of the open frame or the transverse frame members instead of projecting up from the transverse frame members.

The resiliently flexible material of the base member may be a polymeric material that is a polyamide material, for example nylon, or an addition polymer, for example polyethylene or polypropylene, or a condensation polymer, for example polyurethane, or a polycarbonate, or a thermoplastic elastomer, for example santoprene.

In one example form of the invention the base member may be made of nylon and the teeth engaging member may be made of silicon rubber.

The teeth engaging member may include at least one pair of adjacent teeth positioning formations for bearing against and positioning specific teeth within the dentition of the associated arch.

Each pair of adjacent teeth positioning formations may be aligned with each other along the length of the teeth engaging member and may be located on respectively the inner and outer flanges of the teeth engaging member facing into the associated arch receiving channel, being either the upper arch receiving channel or the lower arch receiving channel.

Each adjacent teeth positioning formation may comprise a wedge shaped protrusion having a wedge point facing into the channel away from the inner or outer flange on which it is located. Further adjacent teeth positioning formation of each pair may be integrally formed with the flange on which it is located, e.g. by being moulded integrally with the remainder of the teeth engaging member.

The teeth engaging member may include a first pair of said adjacent teeth positioning formations that are arranged on the midline of the appliance for positioning between the two inner incisors when mounted on a patient.

The teeth engaging member may include a second and third pair of adjacent teeth positioning formations that are arranged to be positioned between the inner and outer incisors on the left side, and between the inner and outer incisors on the right side.

The teeth engaging member may include fourth and fifth pairs of adjacent teeth positioning formations that are arranged to be positioned between the outermost incisor and the canine on the left side, and the outermost incisor and the canine on the right side of the arch of a patient.

The teeth engaging member may include sixth and seventh pairs of adjacent teeth positioning formations that are arranged to be positioned between the canine and the first pre-molar on the left side, and the canine and the first pre-molar on the right side of the arch of a patient. The teeth engaging member may include yet further pairs of adjacent teeth positioning formations for positioning further teeth on the arch of a user.

In those forms of the invention where the teeth engaging member defines both upper and lower channels for receiving the upper and lower dental arches and associated dental structures of a patient, the teeth engaging member may have pairs of adjacent teeth positioning formations in both said upper and lower channels for positioning specific teeth on both the upper and lower arch of the patient.

The orthodontic appliance may also include a tongue tab for encouraging a patient to correctly position their tongue. The tongue tab may be formed on the inner flange of the teeth engaging member and may be positioned above the web.

The teeth engaging member may include at least one cutaway or recess above the web on the inner flange of the teeth engaging member. Conveniently the inner flange may define two cutaways above the web on the inner flange, namely one on either side of the tongue tab.

The teeth engaging member may include at least one further cutaway or recess below the web on the inner flange of the teeth engaging member. The further cutaway may be defined on the midline of the appliance.

The one and further cutaways enable the teeth engaging member provide space when the left and arm regions of the appliance are moved towards each other when the appliance is manually flexed out of its resting form.

The teeth engaging member may include a cut away on the outer flange above the web, and another cutaway on the outer flange below the web. These cutaways are formed in the outer flange so that an underlying region of the soft gum on the associated dental arch of a patient does not make contact with the teeth engaging member when the appliance is mounted on the patient in use.

The web of the teeth engaging member appliance may be formed of varying thickness along its length. In particular the thickness of the web may increase progressively in a direction rearward from the central front region of the appliance towards the free ends thereof. The thickness of the web may increase up to a point of maximum thickness on each arm region that is short of the free ends of the web. Thereafter the thickness of the teeth engaging member may progressively decrease from the point of maximum thickness to the free ends of the web.

The thickening of the teeth engaging member may resemble an inverted aerofoil, e.g. with a curved lower surface and a substantially planar upper surface, when viewed in cross section. By shaping the web region in this way, the teeth engaging member supports the dentition on the upper and lower arches when the upper and lower jaws are brought together.

This encourages relaxation of the muscles, particularly where the user has a malocclusion and there is a space between the occlusal surfaces of the dentition on the upper and lower arches. It also supports the temporomandibular joint (TMJ joint).

Applicant envisages that the orthodontic appliance will be made in several sizes and a suitable size of appliance will be selected for a patient based on the size of their dental arches and associated dental structures. Applicant envisages that the appliance will be manufactured in three or more different arch sizes to accommodate relatively larger arch sizes in patients and relatively smaller arch sizes. Each arch size will be manufactured with six or more variations in the arrangements of the adjacent teeth positioning formations. The different arrangements of the adjacent teeth positioning formations are intended to cater for different teeth sizes and different individual teeth positions in different patients.

According to another aspect of this invention there is provided an orthodontic appliance for promoting development of a dental arch form in a patient who has an underdeveloped arch form, the appliance including:

a base member that is made of a resiliently flexible material having a shape that corresponds generally to a dental arch form, and a teeth engaging member that encloses at least part of the base member and that defines at least one of upper and lower dental arch receiving channels, the teeth engaging member being made of a resiliently flexible material that is more flexible than the resiliently flexible material of the base member and that can be deformed, wherein the appliance comprises a front region and left and right arm regions on either side of the front region, and the front region is formed with a greater stiffness than the left and right arm regions, and the appliance has a resting form in which the resilient materials of the base member and the teeth engaging member are in their resting condition, and when the appliance is deformed out of the resting form to fit the underdeveloped dental arch form into the dental arch receiving channel, the greater stiffness of the front region enables it to exert a greater return force against an anterior region of the dental arch form than the arm regions bearing against other regions of the dental arch form.

The base member may be in the form of an open frame structure comprising a curved outer frame member and a curved inner frame member, and the front region of the appliance may be formed with a greater stiffness that the left and right arm regions thereof by having at least one transverse frame member extending between the inner and outer longitudinal frame members of the base member in said front region.

The at least one transverse frame member extending between the curved inner and the curved outer frame members in the front region, may include a first pair of transverse frame members including one transverse frame member towards one side edge of the front region and a further transverse frame member towards the other side edge of the front region.

The transverse frame members of the first pair may be positioned so that they align with respectively the left and right outer incisors of a patient. The first pair of transverse frame members may each have a width of 1-4 mm, e.g. 2-3 mm.

The base member may include a further transverse frame member extending between the curved inner and outer frame members in the front region of the appliance, to further stiffen the front region of the appliance, the further transverse frame member being positioned between said two transverse frame members making up the first pair.

The further transverse frame member in the front region of the appliance may have a width of 5 to 15 mm, e.g. 8 to 12 mm.

The transverse frame arrangement may further include a second pair of transverse frame members comprising a left rear transverse frame member towards the rear of the left arm region, and a right rear transverse frame member towards the rear of the right arm region thereof.

The transverse frame arrangement may further include a third pair of transverse frame members positioned intermediate the first and second transverse frame members.

This invention also extends to a method of treating a patient to encourage development of an underdeveloped arch form in a patient, the method comprising the steps of fitting an appliance as described in the first or second aspects of the invention above to a patient, and having the patient to wear the appliance on a regular basis.

The method may include encouraging development of the upper arch of a patient by expanding the upper arch form to treat a Class 2 malocclusion.

The method may include aligning the dentition on the underdeveloped dental arch of the patient that is being encouraged to develop.

Having the patient wear the appliance may include having the patient wear the appliance for at least 12 hours in each 24 hour day. Preferably the patient wears the appliance at least 2 hours during the day time and during the night while the patient is sleeping.

DETAILED DESCRIPTION OF THE INVENTION

An orthodontic appliance in accordance with this invention may manifest itself in a variety of forms. It will be convenient to hereinafter provide a detailed description of at least one embodiment of the invention with reference to the accompanying drawings. The purpose of providing this detailed description is to instruct persons having an interest in the subject matter of the invention how to put the invention into practice. It is to be clearly understood however that the specific nature of this detailed description does not supersede the generality of the preceding statements. In the drawings:

FIG. 13 is a three dimensional view of the appliance of FIG. 1 in its resting or original condition prior to use;

FIG. 14 is a schematic three dimensional view of the appliance of FIG. 13 showing how left and right arm regions can be moved towards each other by hand pressure being applied by a patient or a dental practitioner;

Figure 1:
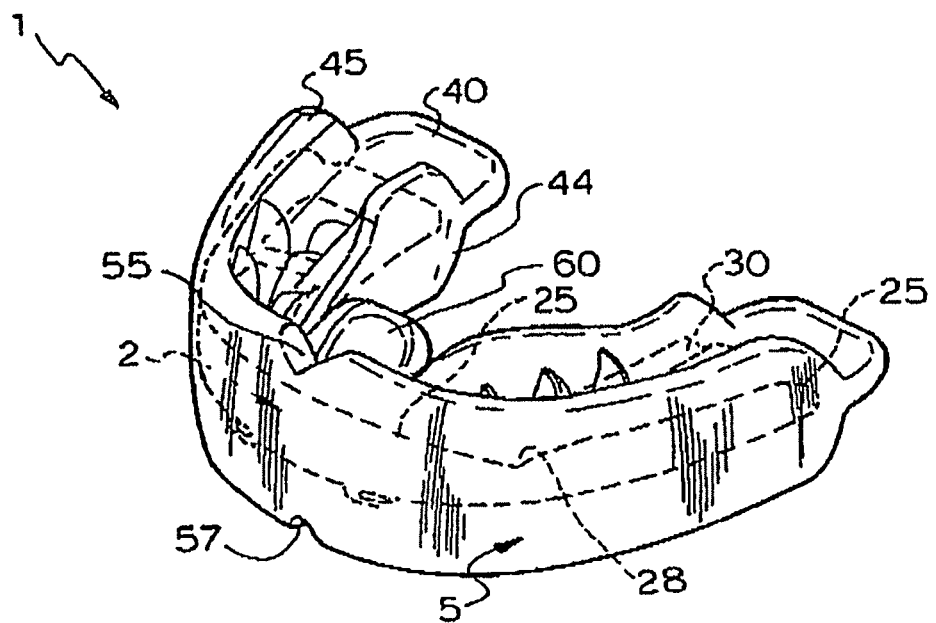
FIG. 1 is an upper three dimensional view of an orthodontic appliance that is an orthodontic appliance in accordance with one embodiment of the invention, viewed from the front.

FIG. 19 shows two schematic profiles of a patient prior to treatment illustrating the effect of incorrect swallowing and mouth breathing on the profile of the patient, and a third schematic profile of a patient after treatment showing the correct positioning of the arches and lips; and FIG. 20 is a schematic drawing showing a plan view of the appliance in its resting from and also showing the appliance in a deformed condition when it is fitted to an underdeveloped arch of a patient.

In FIGS. 1 to 9 a reference numeral 1 refers generally to an appliance that is an orthodontic appliance in accordance with the invention for promoting development of a dental arch form in a patient who has an underdeveloped arch.

The appliance 1 comprises broadly a base member 2 having a shape that corresponds generally to a dental arch form representing correct dental occlusion, i.e. a correct dental bite, and that is made of a resiliently flexible material, and a teeth engaging member 5 that encloses at least part of the base member 2 and defines upper and lower dental arch receiving channels. The teeth engaging member 5 is made of a resiliently flexible material that is deformable and is softer than the resiliently flexible material of the base member 2.

The appliance 1 has a resting form in which the resilient materials of the base member 2 and the teeth engaging member 5 are in their resting condition, and the appliance 1 can be flexed or deformed out of its resting form to fit the underdeveloped dental arch form into the dental arch receiving channel. The appliance 1 when deformed in this way exerts a return force that is directed to returning it to its resting form which drives expansion of the underdeveloped arch to a developed arch form.

The teeth engagement member 5 is made of silicone rubber and occupies a substantially greater volume than the base member 2 and forms the body and shape of the appliance 1. It also defines the contacting surfaces that make contact with and engage the arch and associated dental structures such as the dentition and other tissues of a patient.

Figure 10:
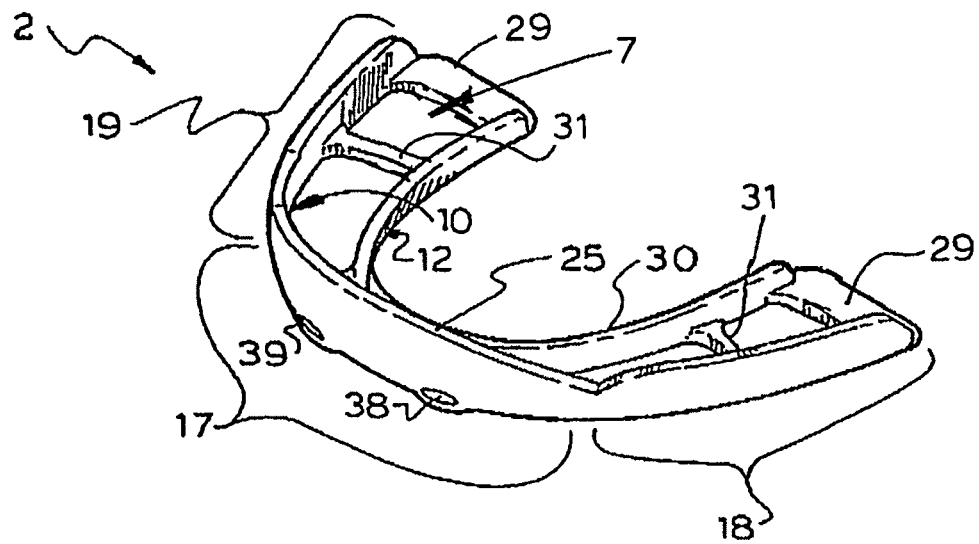
FIG. 10 is an upper three dimensional view of the base member of the appliance of FIG. 9 viewed from the front.
Figure 11:
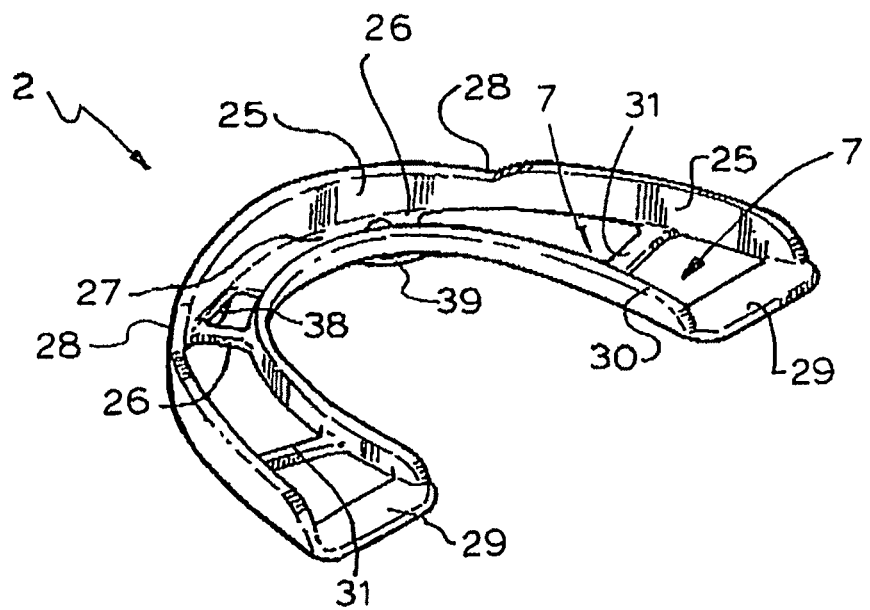
FIG. 11 is an upper three dimensional view of the base member of FIG. 10 when viewed from the rear.
Figure 12:
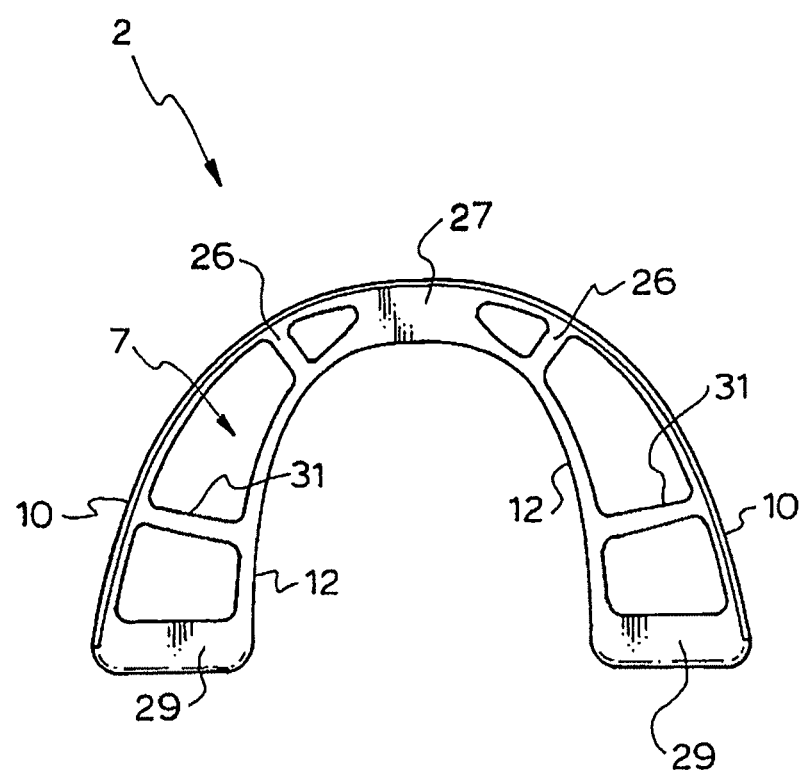
FIG. 12 is a top plan view of the base member of FIG. 10.

The base member 2 is shown in hidden detail lines in FIGS. 1 to 9 and will now be described in more detail with reference to FIGS. 10 to 12 in which it is shown separate from the teeth engaging member 5.

The base member 2 comprises a front region or central frontal portion that is indicated generally by numeral 17. It also includes a left arm region 18 extending away from a left side edge of the front region 17, and a right arm region 19 that extends away from a right side edge of the front region 17. In this specification the terms left and right shall be considered from the point of view of the side of a patient's body that the feature is located on, when the appliance 1 is mounted on a dental arch of the patient. Thus the left arm region 18 will extend along the left side of a patient's arch and the right arm region 19 will extend along the right side of the patient's arch. The front region and the left and right arm regions of the base member correspond broadly to a front region and left and right arm regions of the teeth engaging member and also the appliance 1 as a whole.

The base member 2 is in the form of an open frame structure 7 extending in an occlusal plane comprising a curved outer longitudinal frame member 10 and a curved inner longitudinal frame member 12. The inner frame member 12 broadly follows the curve on the outer longitudinal frame member 10 but is spaced inward of the outer longitudinal frame member 12.

The open frame structure 7 includes a transverse frame member arrangement indicated generally by numeral 15 comprising a plurality of transverse frame members interconnecting the outer and inner longitudinal frame members 10, 12 to form the structure.

The transverse frame member arrangement 15 is designed to stiffen the front region 17 of the base member 2 so that it requires a greater force to resiliently flex the front region 17 than the left ands right arm regions 18, 19 of the base member 2. The front region 17 also exerts a correspondingly greater return force when it is flexed out of its resting position than when the left and right arm regions 18, 19 of the base member 2 are flexed out of their resting position.

The result is that when the front region 17 of the appliance 1 is deformed to fit the appliance to dental arch having a narrowed anterior region with protruding incisors, the front region 17 of the base member 2 and also the appliance 1 as a whole exerts a correspondingly greater return force on the anterior region of the arch than the force applied to other regions of the arch.

The transverse frame arrangement 15 includes a first pair of transverse frame members 26 including one transverse frame member towards one side edge of the front region 17 and a further transverse frame member towards the other side edge of the front region 17. The left and right transverse frame members 26 of the first pair are aligned with respectively the left and right outer incisors of a patient (i.e. the second teeth in the first and second quadrants) when the appliance 1 is fitted thereto as is shown in the drawings. The first pair of intermediate transverse frame members 26 have a width of 1-4 mm, e.g. about 2 mm.

The transverse frame member arrangement 15 also includes a front transverse frame member 27 extending between the inner and the outer longitudinal frame members 12, 10 in the front region 17 of the base member 2. The front transverse frame member 27 is positioned substantially centrally with respect to the base member 2 and extends across part of the two central incisors of a patient. The front transverse frame member 27 has a centre point midway along its length that is aligned with a midline of the appliance as a whole.

The front transverse frame member 27 has a width of about 8 to 12 mm measured from one side edge thereof to the other side edge thereof and is considerably wider than the first pair of transverse frame members 26 of the transverse frame arrangement 15. The additional width serves to confer additional, strength and rigidity in the front region 17 of the base member 2.

The first pair of transverse frame members 26 together with the front transverse frame member 27 together stiffen and rigidify the open frame structure 7 of the base member 2 in the front region 17. This helps the base member 2 to preserve a developed arch form, e.g. expanded arch form, in the anterior region of the appliance 1 when the appliance 1 is deformed causing the arm regions 18, 19 to move towards or away from each other.

The transverse frame arrangement 15 further includes a second pair of transverse frame members 29 comprising a left rear transverse frame member located at the rear end of the left arm region 18, and a right rear transverse frame member at the rear end of the right arm region 19. Each of the left and right rear transverse frame members 29 has a width of 3 to 6 mm.

The transverse frame arrangement 15 further includes a third pair of transverse frame members 31 comprising a left transverse frame member positioned intermediate the left member 26 of the first pair and the left rear member 29, and a right transverse frame member positioned intermediate the right member 26 of the first pair and the right rear member 29. The third pair of intermediate transverse frame members 31 is typically of similar thickness to the first pair of intermediate transverse frame members 26. Each pair of transverse frame members 26, 29, and 31 is arranged in a bilaterally symmetrical fashion about the midline of the appliance as is shown in the drawings.

The third pair of intermediate transverse frame members 31 is positioned adjacent to the first premolars on the dental arch when the appliance is fitted to a patient (e.g. the fourth teeth in the first and second quadrants when viewed in plan view). The third pair of intermediate transverse frame members 31 is thus positioned quite a bit closer to the rear frame members 29 than the first pair of frame members 26 on the front region 17 of the base member 2. This predisposes the section of the base member 2 intermediate the frame members 26 and the frame members 31 to undergo flexing when the appliance 1 is deformed in use.

The base member 2 also includes a teeth row repositioning formation that is an outer flange 25 in the form of a continuous outer wall extending the length of the outer frame member 10 that projects up from the outer frame member 10 and defines an upper edge. The outer flange 25 projects up above the plane defined by the outer and inner members 10 and 12 and the transverse frame members of the transverse frame member arrangement 15 and contribute to the rigidity and stiffness, and torsional rigidity, of the base member 2.

The outer flange 25 comprises a front flange portion extending across the front region 17 of the base member 2 and left and right flange portions extending across the left and right arm regions 18, 19 thereof. The upper edge of the front flange portion extends up to a height of 6-8 mm above the transverse frame members 15. The upper edges of the left and right flange portions are not as high as the left and right flange portions and extend up to a height of 5-7 mm above the transverse frame members 25. The height is measured from the upper surface of a proximate transverse frame member 25 to the upper edge of the inner flange 30. The outer flange 25 forms a continuous wall along the length of the arch and promotes alignment of the dentition of the upper arch of a patient in a row or line along the arch.

The outer flange 25 also defines canine gaps shown by numeral 28 on each side thereof. Each canine gap 28 is formed by having the upper edge of the outer flange 25 descending to a low point intermediate the central front portion 17 and the left and right portions and then ascending upwards again.

The canine gaps 28 on the upper edge of the outer flange 25 are located in the position where the eye teeth or canine teeth of a patient would be located. The canine gaps 28 expose more of the canine teeth when the appliance 1 is being worn so that the outer flange 25 does not need to fit around the canine teeth. Applicant has observed that the canine teeth of a patient are sometimes positioned laterally outward of the other teeth prior to treatment, and the canine gaps 28 permit the canine teeth to project through the gaps and thereby fit the appliance to a patient even where there is considerable misalignment.

In the illustrated embodiment the base member 2 also includes a curved inner flange 30 in the form of a continuous wall projecting up from the inner frame member 12. The inner flange 30 defines an upper edge projecting up to a height that is 1-3 mm, e.g. about 2 mm, above the transverse frame members and is lower and less prominent than the outer flange 25. The height is measured from the upper surface of a proximate transverse frame member 25 to the upper edge of the inner flange 30. The inner flange 30 can also contribute to the rigidity and stiffness the base member 2. The curved inner flange 30 can also assist with aligning teeth in a row along the arch.

The base member 2 in the drawings does not have a flange depending or extending down below either the outer frame member 10 or the inner frame member 12 of the base member 2 to any appreciable extent. Applicant has found that having an outer flange 25 that projects up from the open frame structure 7 but not down there from provides the base member 2 with the necessary level of stiffness. However a flange that also projects downwardly away from the curved outer frame member 10 would further increase the strength of the base member and falls within the scope of this invention.

In another embodiment of the invention that has not been illustrated the orthodontic appliance and specifically the base member thereof does not have an inner flange 30.

The base member 2 defines a pair of openings 38, 39 in its central front region 17 that relate to the moulding process that is used to manufacture the appliance 1. The openings 38, 39 are formed in both the inner and outer curved frame members 12, of the base member 2 on left and right sides of the front region 17 of the base member 2, and are integrally formed in the base member 2. The openings 38, 39 are aligned with corresponding openings in the teeth engaging member 5 as will be described in more detail below.

The teeth engaging member 5 that surrounds and encases the base member 2 will now be described in detail.

Broadly the member 5 comprises a central web 40 and an inner flange 44 and an outer flange 45 (or inner and outer walls) 44, 45 that respectively upwardly and downwardly away from the web 40. These flanges 44, 45 together with the web 40 form an upper channel 46 and a lower channel 47 within which the upper and lower dental arches and associated dentition of a patient are received. The web 40 forms occlusal bite surfaces that bear against the bite surfaces of the dentition of the upper and lower dental arches.

The teeth engaging member 5 comprises a front region 51, and left and right arm regions 48 and 49 corresponding to the front region 17 and left and right arm regions 18 and 19 of the base member 2. The front region 51 of the teeth engaging member 5 is mounted over and encases the front region 17 of the base member 2 and has the same extent as the front region 17 of the base member 2. That is the side edges of the front regions 17, 51 of respectively the base member 2 and the teeth engaging member 5 broadly coincide.

The front region of the appliance is basically the same as the front region of the teeth engaging member 5 and the left and right arm regions of the appliance are basically the same as the left and right arm regions of the teeth engaging member 5. The left and right arm regions 48, 49 have a greater longitudinal extent than the left and right arm regions of the base member 2 as shown in the drawings and particularly in FIGS. 2, 5 and 6. That is the rear edges of the teeth engaging member 5 are spaced rearward of the rear edges of the base member 2.

The teeth engaging member 5 fills in the space between the inner and outer longitudinal frame members 12, 10 and the transverse frame members 26, 27, 29 and 31 also forms a layer having some thickness above and below the inner and outer frame members 12, 10.

Figure 2:
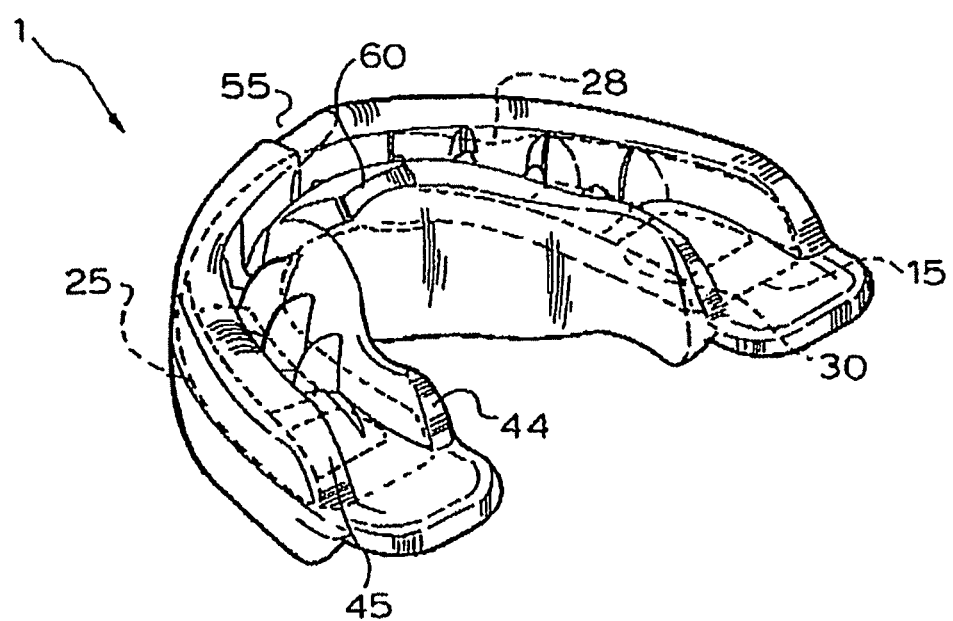
FIG. 2 is an upper rear three dimensional view of the appliance of FIG. 1, viewed from the rear.
Figure 3:
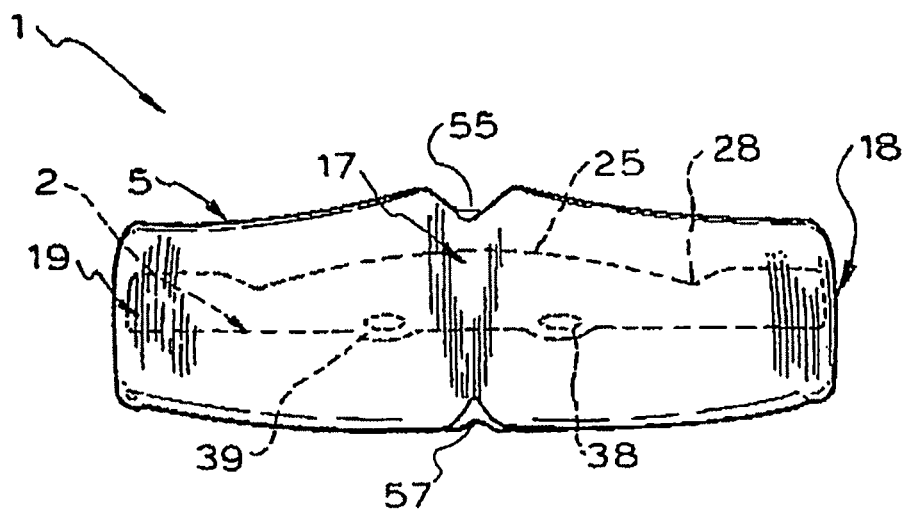
FIG. 3 is a front view of the appliance of FIG. 1.
Figure 5:
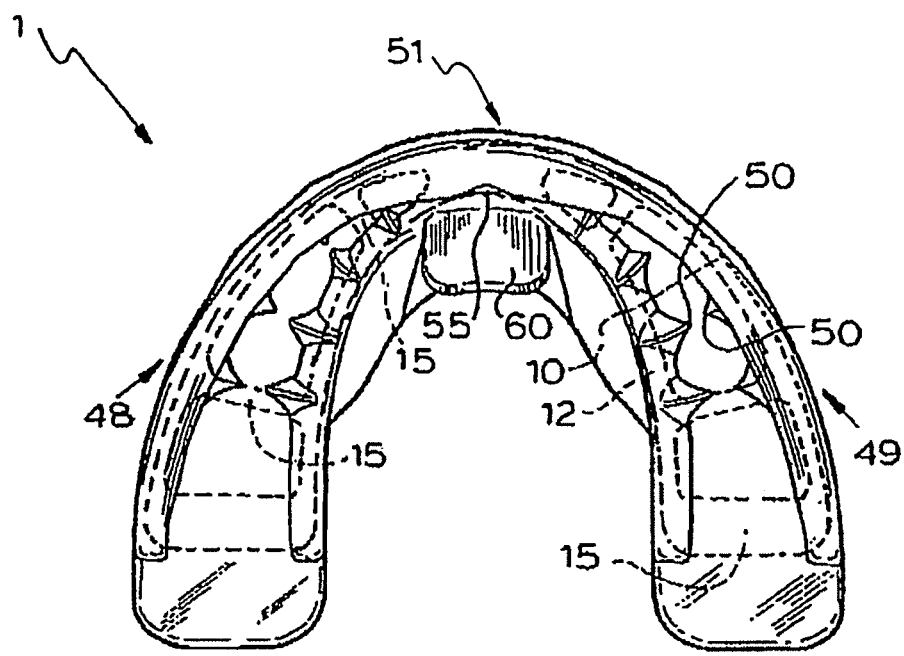
FIG. 5 is a top plan view of the appliance of FIG. 1.
Figure 6:
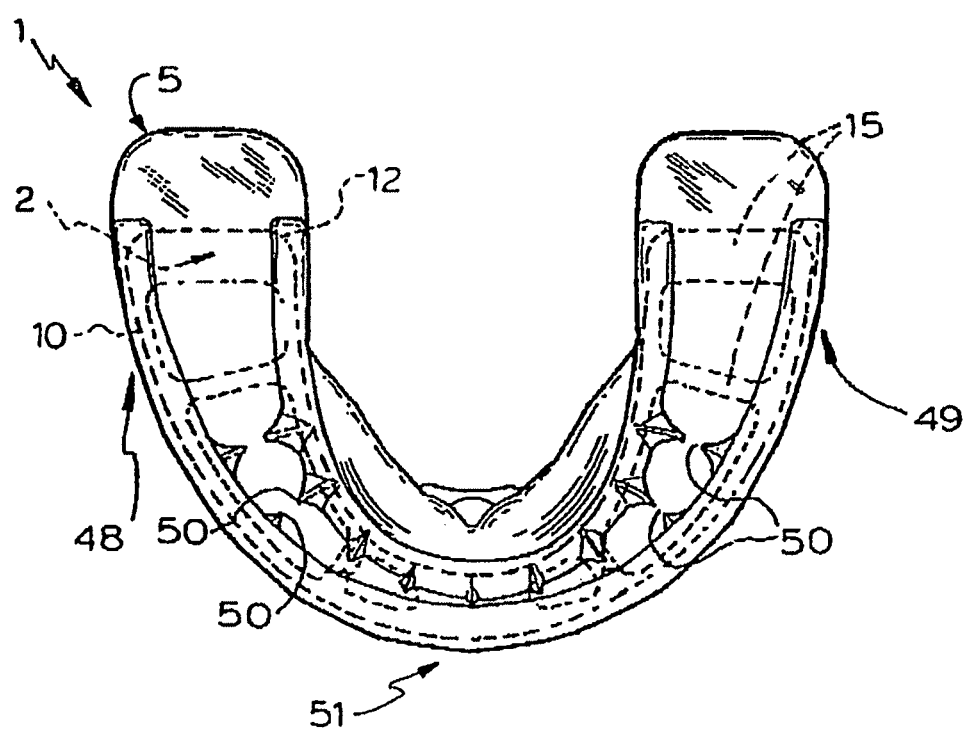
FIG. 6 is a bottom plan view of the appliance of FIG. 1.
Figure 7:
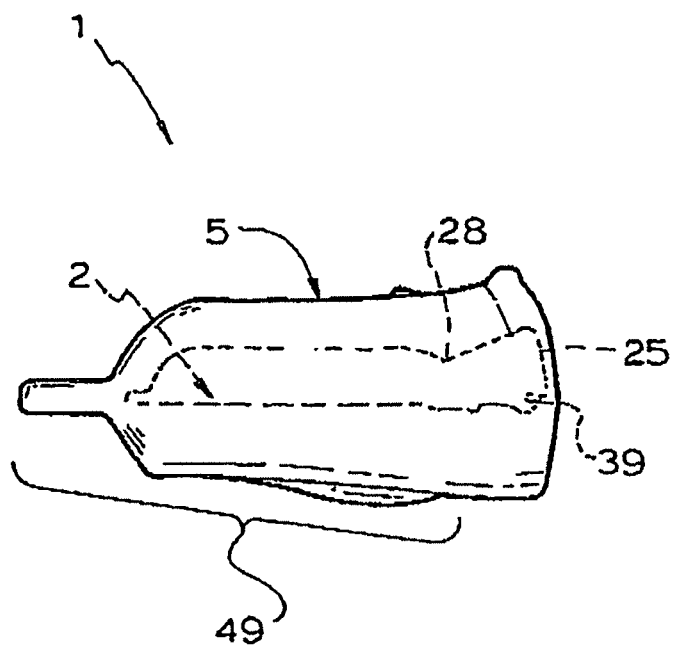
FIG. 7 is a side view of the appliance of FIG. 1 from one side.
Figure 8:
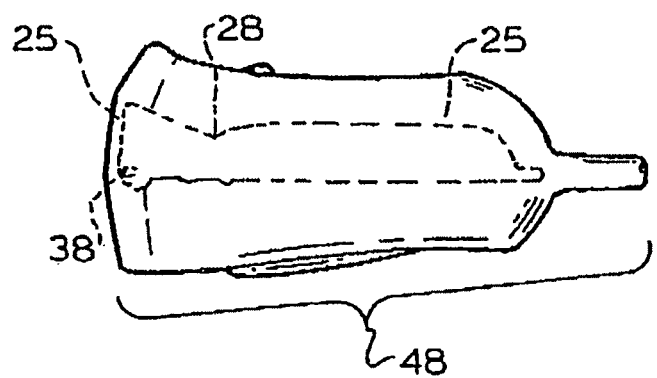
FIG. 8 is a side view of the appliance of FIG. 1 from the other side.
Figure 9:
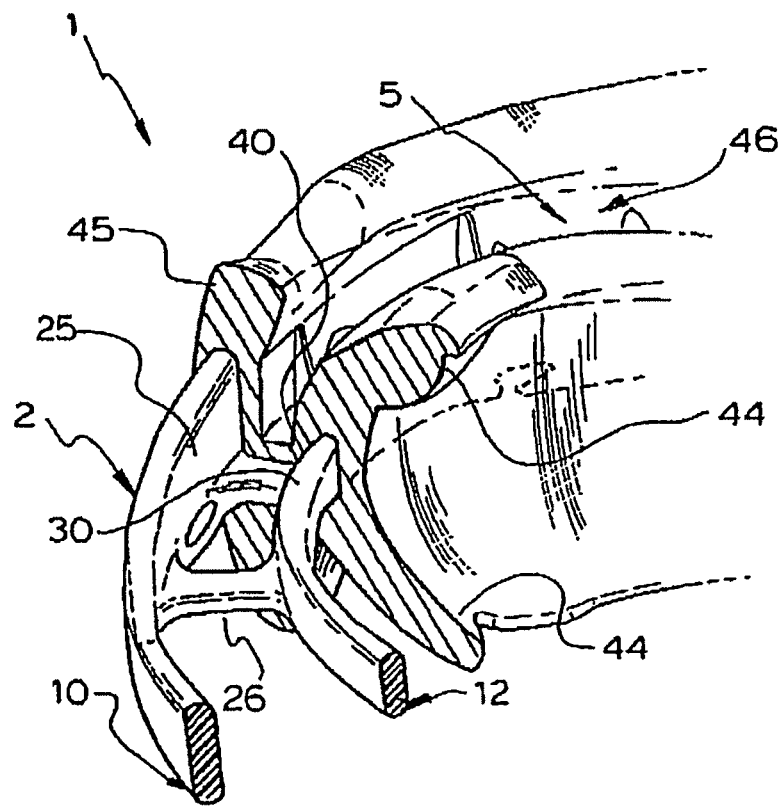
FIG. 9 is an upper three dimensional view of part of the appliance of FIG. 1 with part of a teeth engaging member thereof removed to expose an underlying base member.

The left and right arm regions 48, 49 have a greater longitudinal extent than the left and right arm regions of the base member 2 as shown in the drawings and particularly in FIGS. 2, 5 and 6. That is the rear edges of the teeth engaging member 5 are spaced rearward of the rear edges of the base member 2.

The appliance 1 also includes an adjacent teeth positioning arrangement shown generally by reference numeral 50 on the inner and outer flanges 44, 45 of the teeth engaging member 5 for assisting in positioning specific teeth in certain positions along the line of the arch.

Specifically the adjacent teeth positioning arrangement 50 comprises a plurality of pairs of adjacent teeth positioning formations. Each pair of positioning formations comprises a first positioning formation on the outer flange 45 of the member 5 projecting from the channel surface thereof into the upper dental arch channel, and a second positioning formation on the inner flange 44 of the member 5 projecting from the channel surface thereof into the upper arch channel. The first and second positioning formations in each pair are aligned with each other in a lengthwise direction along the channel.

Each teeth positioning formation within each pair comprises a protrusion that extends away from the surface of the flange on which it is located to a terminal free end that is spaced away from the channel surface. The positioning formations are wedge shaped when the appliance is viewed in plan view tapering inwardly from both sides on the surface of the flange to a wedge point. The wedge point extends in a line broadly transverse to the plane of the web of the member 5 as is shown in the drawings. That is the terminal free end is broadly vertically extending when the appliance is fitted to a patient and is designed to fit into the interproximal space between two adjacent teeth on an arch in use. The first and second positioning formations of each pair are integrally formed with the flange on which they are located when the member is moulded during its manufacture.

In the illustrated embodiment the adjacent teeth positioning arrangement 50 has nine pairs of adjacent teeth positioning formations on the upper channel for interacting with the upper dental arch structures of a patient.

This arrangement includes a first pair of said adjacent teeth positioning formations that are arranged on the midline of the appliance for positioning between the two central incisors when mounted on a patient. It also includes a second and third pair of adjacent teeth positioning formations are arranged to be positioned between the central and outer incisors on the left side, and between the central and outer incisors on the right side. It also includes fourth and fifth pairs of adjacent teeth positioning formations are arranged to be positioned between the outermost incisor and the canine on the left side, and the outermost incisor and the canine on the right side of the arch of a patient. It also includes sixth and seventh pairs of adjacent teeth positioning formations are arranged to be positioned between the canine and the first pre-molar on the left side, and the canine and the first pre-molar on the right side of the arch of a patient. It also includes eighth and ninth pairs of adjacent teeth positioning formations are arranged to be positioned between the first pre-molar and the second molar on the left side, and the first pre-molar and the second molar on the right side of the arch of a patient.

In the illustrated form of the invention where the teeth engaging member 5 defines both upper and lower channels for receiving the upper and lower dental arches and associated dental structures of a patient, the teeth engaging member 5 includes a similar arrangement of pairs of adjacent teeth positioning formations on the inner and outer flanges and projecting into the lower channel for receiving the lower dental arch and associated dental arch structures of a patient.

The adjacent teeth positioning formations 50 are for biasing individual teeth into specific teeth positions on the dental arch of the patient. The pairs of adjacent teeth positioning formations are positioned so that they insert between adjacent teeth on the dental arch when the appliance is mounted on the dental arch. The wedge shape tends to urge teeth apart from each other and to form a space between adjacent teeth. The pairs of teeth positioning formations urge the adjacent teeth apart from each other and thereby form a space between the adjacent teeth. The adjacent teeth positioning formations are located in the anterior region of the arch and thus they work to form spaces between adjacent teeth in the anterior region of the dental arch.

As the teeth on the dental arch are generally in end to end contact when the treatment commences, the arch needs to expand to create additional space for spaces between the adjacent teeth to be formed. The teeth positioning formations project into the space between adjacent teeth and push them apart which in turn encourages the arch to expand to provide the extra space. The teeth positioning arrangements thereby also subtly encourages the arch to expand in addition to the arch developing force of the deformed appliance fitted to a patient as described above. The teeth positioning formations also help to position individual teeth in specific positions along the length of the arch.

In the illustrated example the orthodontic appliance also includes a notch or cut-out 55 in the midline of the upper surface of the outer flange 45. It also includes a smaller midline notch or cut-out 57 in the lower surface of the outer flange 45. The notches 55, 57 form a recess or gap on the appliance midline so that the member 5 does not come into contact with soft tissue in the area of the dental midline. There is a tendon that extends across the dental midline and the appliance 1 can be more comfortably worn by a patient if the teeth engaging member 5 does not come into contact with this tendon. The recesses 55, 57 avoid contact with this tendon.

The orthodontic appliance 1 also has a tongue tab 60 for positioning the tongue of a patient in an exact central position. The tongue tab is formed in the inner flange 44 of the member 5 upwardly of the web 40. This trains a patient to correctly position their tongue to improve their oral habits and particular to avoid tongue thrusting.

Figure 4:
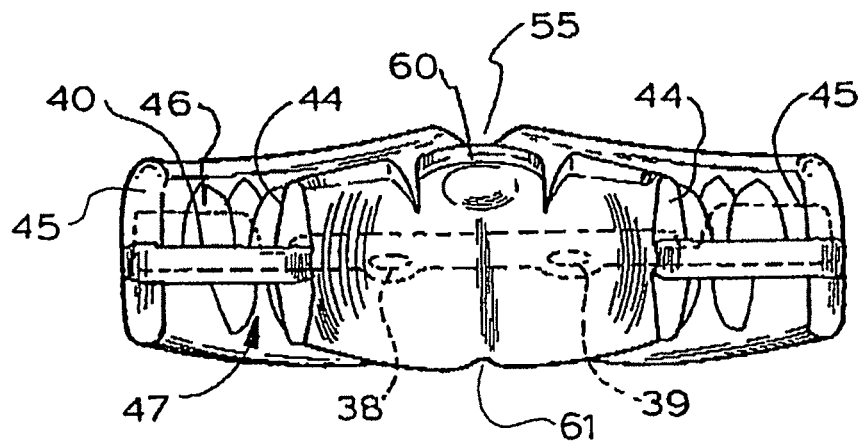
FIG. 4 is a rear view of the appliance of FIG. 1.

The inner flange 44 defines gaps on either side of the tongue tab 60 as shown in FIG. 4. The inner flange also defines a small notch or cutaway 57 formed in the lower edge of the inner flange as shown in FIG. 4. These spaces help to facilitate inward and outward adjustment of the arm regions 48, 49 of the teeth engaging member 5 of the appliance 1 to enable it to be fitted to an underdeveloped arch.

Further the occlusal surfaces of the web 40 of the teeth engaging member 5, e.g. upper and lower faces thereof, taper outwardly from the front region 51 of the member 5 in a rear direction to the left and right trailing arm regions 48, 49. The effect of this is to progressively thicken the web 40 in a direction from the front to the rear of the teeth engaging member 5. This continues up to a point in the left and right trailing arm regions 48, 49 that is spaced forward of the rear ends of the arm regions. Thereafter the upper and lower faces of the engaging member 5 taper inwardly towards each other so as to progressively thin from said point to the rear of the teeth engaging member 5. In summary the web 40 can generally be described as having an inverted asymmetric aerofoil shape on each arm region 48, 49 extending in a direction rearward from the front region 51. The aerofoil is inverted and has a curved surface on its lower side.

This aerofoil shape of the web 40 fills in any space that exists between the upper and lower teeth of a patient as a result of malocclusion and supports the jaw. This enables the lower jaw to assume its anatomically correct position in relation to the upper jaw. This supports the dentition in cases where the occlusal surfaces of the dentition of the upper and the lower arches are spaced from each other and helps the patient to relax and not clench their jaw. It also confers other muscular benefits on the patient.

The teeth engaging member 5 also has passages defined therein in the same place as the apertures 38, 39 of the base member 2. These passages are continuous and open at both ends. The openings 38 and 39 defined in the base member 2 increase the surface area of the teeth engaging member 5 in contact with the base member 2. This assists in moulding the teeth engaging member 5 onto the base member 2.

During manufacture of the orthodontic appliance the base member 2 is injection moulded in a first injection moulding step, and the teeth engaging member 5 is then moulded around the base member 2 in a second moulding step.

The base member 2 is made of a polymeric material having suitable physical properties of stiffness and resilient flexibility to enable the appliance to perform its orthodontic function. In the illustrated embodiment the base member is made of a polyamide material that is nylon. Nylon is a generic name of any long chain synthetic polymeric amide which has recurring amide groups as an integral part of the main polymer chain. The polymer is linear and as such is suited to being formed into a filament although it can also be used to form a three dimensional body. Nylon has been found to have an appropriate level of rigidity yet the base member as a whole is resiliently flexible and can be resiliently flexed out of its resting form so that the left and right arm regions of the base member can be moved towards and away from each other. It also permits some twisting of the left and right arm regions relative to each other.

Further when silicon rubber is used as the material for the teeth engaging member it is able to withstand the injection temperature of silicone when it is injected onto the base member to form the teeth engaging member.

Applicant has obtained Nylon from Shinko Chemical Company based in Taipei, Taiwan. The table below indicates the different grades of Nylon 66 supplied by this company.

| | | | | | | | |
|---|---|---|---|---|---|---|---|
| TENSILE STRENGTH | Kg/cm$^2$ | 800 | 900 | 1700 | 1900 | 840 | 1150 |
| ELONGATION | % | 55 | 10 | 7.1 | 2 | 4 | 4.5 |
| FLEXURAL STRENGTH | Kg/cm$^2$ | 1000 | 1350 | 2300 | 2600 | 1200 | 1700 |
| FLEXURAL MODULUS | Kg/cm$^2$ | 28000 | 35000 | 80000 | 108000 | 31000 | 72000 |
| IZOD IMPACT STRENGTH | Kg-cm/cm | 13 | 8.5 | 11 | 9 | 7.3 | 7 |
| ROCKWELL HARDNESS | R-SCALE | 118 | 119 | 120 | 120 | 118 | 119 |
| MELTING POINT | °C. | 260 | 260 | 255 | 260 | 260 | 260 |
| M.D.T (18.6 kG/cm2) | °C. | 66 | 200 | 238 | 240 | 73 | 248 |
| M.D.T (4.6 kG/cm2) | °C. | 230 | 240 | 255 | 255 | 230 | 245 |
| ASH CONTENT | W1% | | 13 | 33 | 45 | — | 25 |
| MOLD SHRINKAGE | | 1.7-1.8 | 0.3-0.5 | 0.2-0.4 | 0.2-0.3 | 1.0-1.3 | 0.3-0.5 |
| | | 1.3-1.4 | 0.8-1.0 | 0.7-1.0 | 0.3-0.5 | 0.7-1.0 | 0.7-1.0 |
| M.F. | g/10 min | 55 | 20 | 13 | 10 | 43 | 20 |
| SP Gr | g/cm$^2$ | 1.1 | 1.2 | 1.35 | 1.46 | 1.16 | 1.38 |

A grade of Nylon can be used having a tensile strength 800-1000, e.g. about 900, a flexural Strength 1000-1500, e.g. about 1350, and a ROCKWELL Hardness of 90-150, e.g. about 119. In particular Applicant has used a grade of nylon known as Nylon 66 6212GA for the manufacture of appliances in accordance with this invention.

A suitable nylon material can also be obtained from other chemical suppliers such as E I. Du Pont Nemours Chemical Company (Du Pont) based in Delaware in the USA and other suppliers.

In the illustrated embodiment the teeth engaging member is formed of a silicone rubber. A medical grade silicon rubber that is a basic commodity that can be obtained from a number of suppliers such Du Pont Chemical Company based in Delaware in the USA. Applicant has sourced a suitable silicone rubber from a Japanese chemical company by the name of Shin-Etsu Chemical Co Ltd based at 6-1, 2 Chome, Ohtemachi, Chiyodaku, Tokyo, Japan. The material specification data sheet provided by Shin-Etsu for this material is provided below.

MATERIAL SPECIFICATION DATA SHEET

| SHIN-ETSU ® | | | Transparent High Strength | | |
|---|---|---|---|---|---|
| TWO-COMPONENT SILICONE RUBBER COMPOUND | | | KE-1950-50 | KE-1950-60 | KE-1950-70 |
| Typical Properties | | Units | (A-B) | (A-B) | (A-B) |
| Viscosity in mPa · s (P) Brookfield-type rotational viscometer | | | 680 (6800) | 730 (7300) | 750 (7500) |
| Specific Gravity at 25° C. (77° F.) | | g/cm$^3$ | 1.13 | 1.14 | 1.15 |
| Mixing Ratio A:B | | | 1:1 | 1:1 | 1:1 |
| Hardness | JIS-A | | 50 | 58 | 68 |
| Tensile Strength | JIS-6301 | Mpa | 9.3 | 7.8 | 7.8 |
| Elongation at break | JIS-6301 | % | 55 | 380 | 350 |
| Tear Strength | JIS-6301 | kN/m | 44.1 | 43.1 | 49 |
| Compression set | 22 h/150° C. | (%) | 28 | 22 | 50 |

-continued

MATERIAL SPECIFICATION DATA SHEET

| SHIN-ETSU ® | | | Transparent High Strength | | |
|---|---|---|---|---|---|
| TWO-COMPONENT SILICONE RUBBER COMPOUND | | | KE-1950-50 | KE-1950-60 | KE-1950-70 |
| Typical Properties | | Units | (A-B) | (A-B) | (A-B) |
| Linear Shrinkage | JIS-6301 | (%) | 2 | 1.9 | 2.1 |
| Volume Resistivity | Comments | Ω-m | 10T | 10T | 10T |

The silicone rubber used to make the orthodontic appliance can have the following properties:
Hardness of 50-68 according to JIS-A;
Tensile strength of 7.8 to 9.3 Mpa according to JIS-6301;
Elongation at break 55 to 350% according to JIS-6301;
Tear strength of 43.1 to 49 KN/m according to WS-6301;
Applicant has used the hardest grade of silicon extensively, namely KE-1950-70 supplied by Shin-Etsu.

Another supplier of silicone rubber is the Bayer Chemical Company based in Leverkusen, Germany. Bayer supplies a liquid silicone rubber LSR 2050 that is non toxic and suitable as a medical grade material. It is a two component rubber with each component packed in a separate container. These two components are pumped into a static mixer and mixed thoroughly and then injected into the injection mould die.

In the actual moulding of the orthodontic appliance 1 the base member 2 and the teeth engaging member 5 can be moulded in a co-injection moulding process. The base member 2 is moulded in a first step by an injection moulding process and then the teeth engaging member 5 is moulded onto the base member 2 in a second moulding step. The base member 2 does not have to be removed from the mould for the teeth engaging member 5 to be moulded onto it. The mould comprises two mould parts, a first mould part for the base member 2 and a second mould part for the teeth engaging member 5 and the teeth engaging member 5 is moulded directly onto the base member 2 without it being removed from the mould.

During the moulding operation the first mould part is mounted in an operative moulding position in a moulding zone in a first moulding step. Thereafter molten nylon is injected into the first mould part in a first moulding step to form the base member 2. Thereafter the first moulding part is withdrawn from the moulding zone and the second moulding part is moved into its operative position in the moulding zone. Thereafter molten silicon rubber is injected into the second mould part in a second moulding step to mould the teeth engaging member onto the already moulded base member that is received within the second moulding part. The second moulding part is then withdrawn to reveal the newly moulded appliance with the base member encased within the teeth engaging member. Generally the formed orthodontic appliance 1 can be removed from the die once the moulded silicon rubber material has had an opportunity to cool sufficiently for it to be handled.

The cycle times for each of the moulding steps is typically about 15 seconds. The cycle time for the silicone rubber moulding is longer than that for the nylon base member. Generally the moulded pieces are allowed to cool passively. However the silicone rubber which is moulded at a high temperature can be actively cooled once it has been moulded. Generally the formed orthodontic appliance 1 can be removed from the die once the moulded silicon rubber material has had an opportunity to cool sufficiently for it to be handled.

The molten silicone is introduced to the die at a very high temperature and therefore the moulded base member has to be able to withstand this temperature. Nylon is capable of withstanding the injection temperature of silicone and this property as well as its other physical properties that make it suitable for use in the base member of the appliance.

In another form of the invention the appliance can be moulded in two separate dies with the base member being moulded in a first die then the base member can be removed and be placed in a second die where the teeth engaging member is moulded onto the base member 1.

In use the orthodontic appliance 1 described above will typically be initially fitted by an orthodontist or a dentist.

A first step in fitting an appliance 1 is to choose an appropriately sized appliance from the different sizes of appliances. The range of appliances 1 envisaged by the Applicant will have at least three different sizes of base member defining the basic arch form. Each of these base member sizes will then have at least four different sizes of teeth engaging member some of which have an adjacent teeth positioning arrangement thereon and others which do not have a teeth positioning arrangement. Generally an orthodontist will choose a size of appliance after inspecting and measuring the dental arch and associated dental arch structures of the patient using a suitable measuring device that is supplied to the dental practitioner.

Figure 15:
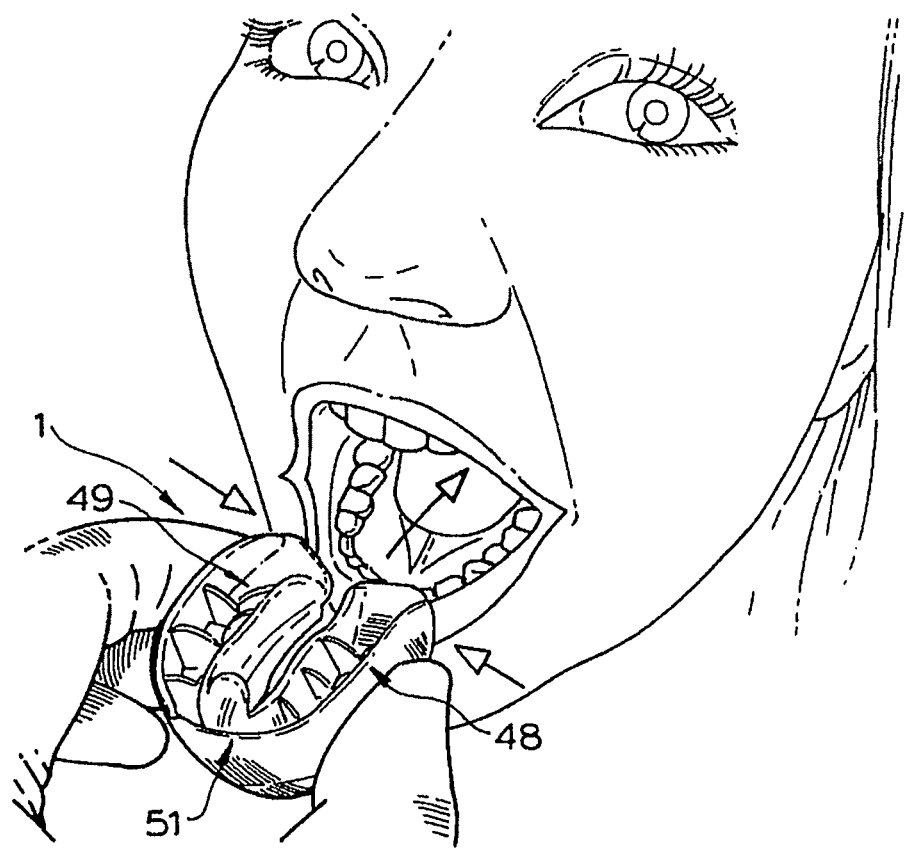
FIG. 15 is a schematic three dimensional view of the appliance of FIG. 13 showing a dental practitioner fitting the appliance to a patient having an underdeveloped arch with the dentist squeezing the left and right arm regions towards each other to fit the appliance over the underdeveloped dental arch of the patient.
Figure 17:
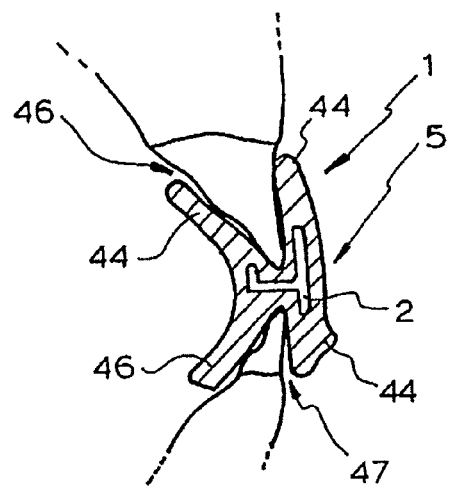
FIG. 17 is a schematic sectional side view of the appliance fitted to the upper arch of a patient along a dental midline.

This procedure of fitting the appliance to a dental arch of a patient is shown schematically in FIGS. 13 to 15. Where the patient has an under developed arch structure such as that found in a class 2 malocclusion, the dentist will manually flex the left and right arm regions 48, 49 of the teeth engaging member 5 and base member 2 towards each other. This movement of the arm regions enables the appliance 1 to be narrowed to the point where it can be fitted over the upper dental arch with a tight fit and a tight grip which is shown schematically in FIG. 17. The silicone rubber is also resilient and can be deformed together with the base member when the appliance is deformed to fit it to an underdeveloped arch.

The soft silicone rubber of the teeth engaging member 5 is in contact with and bears against the dental structures including the gums and teeth of the patient. The silicon rubber cushions the underlying force being applied by the deformed base member so that the appliance is reasonably comfortable to wear despite the return force that is being applied to the arch to encourage expansion of the arch.

The inner and outer flanges 44 and 45, and the occlusal surfaces of the web 40 of the teeth engaging member 5, bear against the upper and lower dental arches and the associated arch structures. The teeth engaging member 5 transmits the force generated by the appliance 1 being flexed out of its resting form through to the dental arch and associated dental structures of the patient.

The underlying rigidity of the base member 2 in particular generates a force that bears against the dental arch and associated dental structures of the patient that have a physiological influence on the bone development of the dental arch form that drives expansion of the arch form. The dental arch form is encouraged to develop into an arch form corresponding to the resting form of the appliance 1 which corresponds to a developed arch form that is conducive to correct dental occlusion. Applicant regards the resilient force that is generated by the base member when it is deformed out of its original shape and which is applied through the appliance to the dental arch as being analogous to active spring energy.

Figure 16:
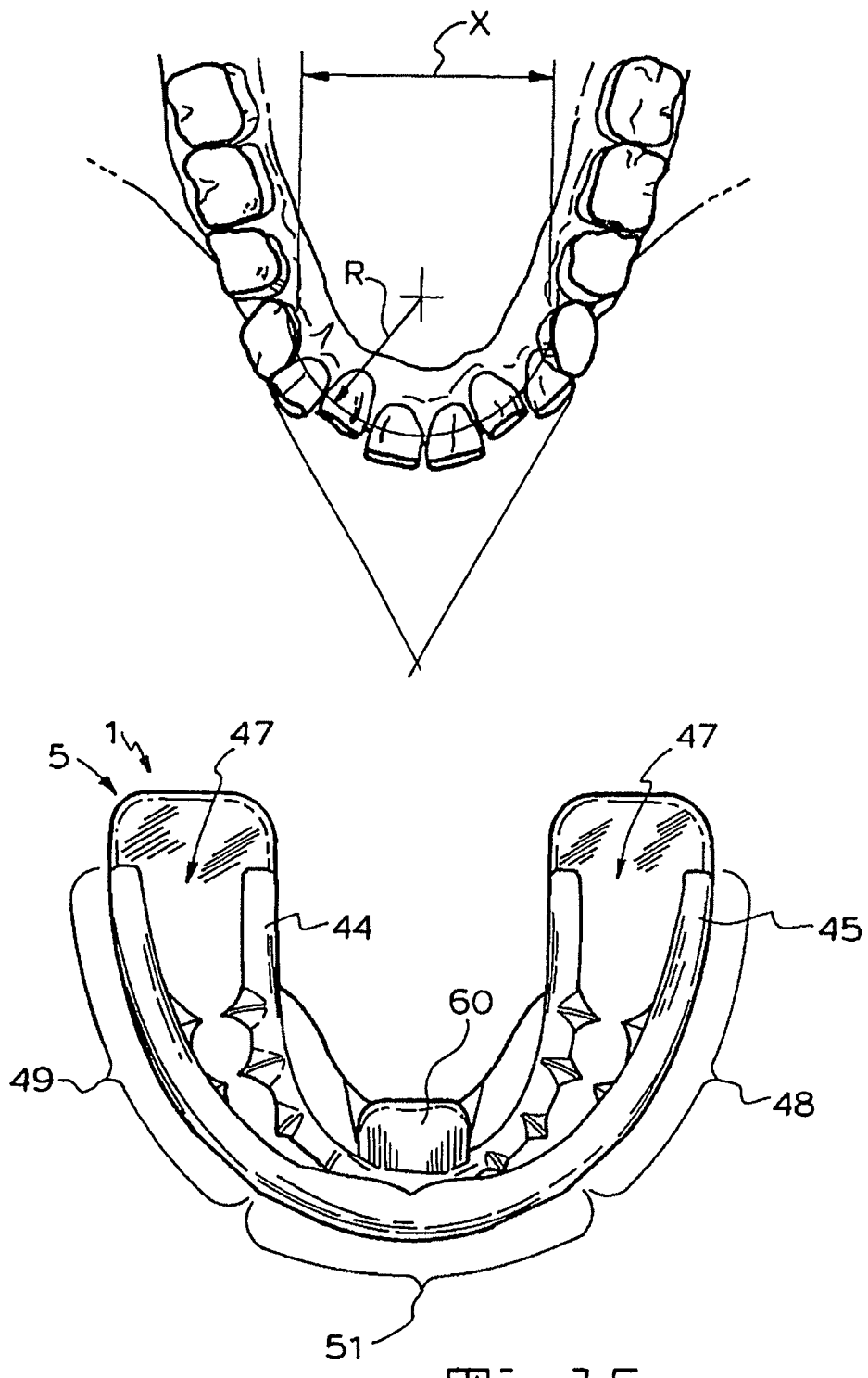
FIG. 16 is a schematic top plan view of the appliance of FIG. 13 in a resting state positioned next to a dental arch of a patient having an underdeveloped arch that is typical of a class 2 malocclusion.

FIG. 16 show an appliance in its original shape next to an underdeveloped dental arch that requires expansion into a more developed arch form. The drawings clearly show how the arch form of the appliance 1 is noticeably wider than the dental arch of the patient. Consequently the appliance 1 has to undergo significant deformation, and specifically a movement of the arm regions towards each other to fit the appliance 1 over the underdeveloped arch form of the patient. The deformation causes the appliance 1 to exert a buccally directed return force against the dental arch and associated dental structures of the patient.

Figure 18:
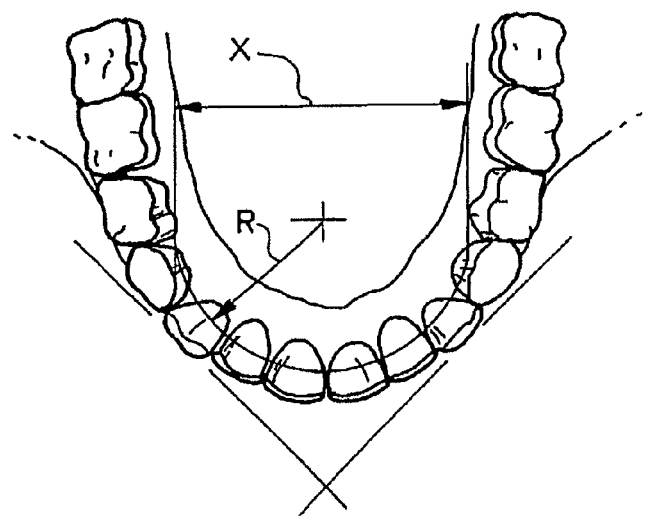
FIG. 18 shows the arch shown in FIG. 16 after the orthodontic treatment of the patient has progressed to the point where the patient's arch has undergone some development.

Over time this force will encourage progressive expansion of the arch and it will become progressively develop an arch form that is more similar to the resting form of the appliance. FIG. 18 shows the arch of the patient of FIG. 15 after it has undergone treatment with the oral appliance and the anterior region of the arch has widened into a developed arch form.

The distance X between the inner surface of the left and right canine teeth in FIG. 18 is much greater than that in FIG. 16. Further the radius of curvature of the line of teeth in the anterior portion of the arch in FIG. 18 shown by R is much greater than that in FIG. 18 thereby showing clearly how the treatment develops the arch and in particular expands the anterior region of the arch.

In addition to influencing arch development on the patient the orthodontic appliance 1 and particularly the teeth engaging member 5 thereof is in contact with the dentition and applies an aligning force to the dentition on the arch. As the appliance 1 has channels that are arranged in a neat curve, the appliance 1 will influence the dentition to align along a similar curve. The rigidity of the base member 2, and in particular the continuous outer flange on the base member 2, contributes to alignment of the dentition on the arch by encouraging protruding and retruding teeth to move to their desired position received within the relevant channel. The teeth are moved into a position between the inner and outer walls or flanges 44, 45 of the teeth engaging member 5 thereby aligning the teeth with other teeth in the row. Thus the use of the appliance over a period of time also assists with the alignment of teeth in a row along the arch. The application of force to move teeth is standard practice in orthodontics and the physiological mechanism by which tooth movement is accomplished is understood by the dental and orthodontic community and will not be described in this specification.

Further the adjacent teeth positioning arrangement 50 on the teeth engaging member 5 also encourages individual teeth to adopt a certain position along the line of the arch.

The orthodontic appliance is a removable appliance that is worn for a number of hours each day and is not worn by a patient at other times of the day. The appliance should be worn for a few hours in the day time when this is possible. The appliance should also be worn each night by a patient while they are sleeping. This extent of usage is sufficient to carry out the treatment effectively. As the appliance has both upper and lower channels that receive both the upper and lower dental arches of a patient, it is not suitable for being worn while the patient is carrying out certain activities. For example a patient could not talk or eat while they were wearing the appliance. Over time with proper use of the appliance and good patient compliance, the application of force by the base member that has been deformed out of its original shape will cause the arch to develop. Once the arch widens crowding of teeth will diminish and the forces generated by the appliance 1 will encourage the teeth to align with each other along the arch.

FIG. 19 shows a sequence of schematic profiles of a patient showing how their profile develops with the progression of treatment with the orthodontic appliance. The first two drawings show the effect of incorrect swallowing and mouth breathing on the profile of the patient. This is evident in the relative positioning of the upper and lower arches and the lip profile. The third drawing shows the profile of the patient after treatment has been completed. The upper and lower arches are correctly positioned relative to each other in the third drawing and the lips are together.

FIG. 20 is a schematic drawing showing a plan view of the appliance in a resting condition and then also showing how the appliance can be deformed to fit it to an underdeveloped dental arch of a patient. In the schematic drawing the patient has an underdeveloped upper arch that needs to be expanded, particularly in the anterior region thereof. The front region of the appliance in particular is flexed and deformed to fit the appliance to the arch. The front region has a greater stiffness than the left and right arm regions of the appliance as has been described above. Consequently when deformed, the front region exerts a return force that is related to the force required to flex it out of its resting condition and this return force is applied to the underdeveloped arch of a user and encourages it to develop. This force is greater than the force applied by the arm regions when they undergo a corresponding amount of deformation. The arrows on the schematic drawing indicate schematically the direction and the strength of the return force that is applied by the deformed front region of the appliance. The longer arrows in the front region shown in the drawings show that the return force applied by the deformed front region is greater than the return force applied by the arm regions when flexed. The strong return force applied by the front region of the appliance encourages the anterior region of the dental arch corresponding to the incisors and the canines to develop.

In another embodiment of the invention that has not been illustrated in the drawings, the base member 2 is made out of nylon and the teeth engaging member is made of polyvinylchloride (PVC). PVC resin is a staple commodity that is supplied by a number of chemical manufacturers including IMPRODEX which is a division of Pacific Dunlop Limited based at 135 Racecourse Road, Flemington, VIC, Australia. The specification for the product used by the Applicant is HYCO 4016-89 PVC compound. Applicant has used a clear extrusion grade PVC compound for the appliance which is supplied by IMPRODEX as their HYCO 4016-89 PVC compound. The properties of this PVC grade are as follows:

| SPECIAL PROPERTIES | |
|---|---|
| Shore A Hardness (ASTM 2240) Instantaneous | 79 |
| Shore A Hardness (ASTM 2240) 10 second delay | 71 |
| Specific Gravity | 1.22 |
| Tensile Strength | 17.7 Mpa |
| Elongation at Break | 400% |

An appliance in which PVC is substituted for silicon is manufactured by a similar two step moulding process to that described above. The base member is moulded of nylon in a first step and then the teeth engaging member is moulded of PVC in a second moulding step. An advantage of using PVC instead of silicone rubber is that it does not require as high an injection temperature as silicon rubber when it is moulded. This reduced injection temperature reduces the mould temperature that the mould equipment and also the material of the base member must be designed to withstand when the molten PVC is injected into the mould. This opens up the possibility of using materials other than nylon for the base member. Applicant envisages that addition polymers, e.g. such as polyethylene, and polypropylene could also be used. Applicant also envisages that condensation polymers such as polyurethane and polycarbonate and a thermoplastic elastomer such as santoprene could also be used because they have a suitable amount of stiffness or rigidity and when they are formed into a base member. The left and right arm regions thereof would be able to be moved towards and away from each other. Further Applicant believes that other thermoplastic materials could also be found to meet these requirements and to be suitable.

In use an orthodontic appliance with a member 5 made of PVC is used in the same way as the appliance described above with reference to FIG. 1. Further the appliance functions in exactly the same way when fitted to the dental arch and associated arch structures of the patient.

An advantage of the appliance described above with reference to the drawings is that it can apply an orthodontic force when it is deformed out of its resting condition that directs it to return to its resting condition. The force is strong enough to encourage an underdeveloped arch on a patient that is typical of a class 2 malocclusion to develop over time with ongoing use of the appliance into a more fully developed arch form that is conducive to a correct dental occlusion. The force that is applied to the teeth is comparable to that achieved by other orthodontic appliances.

The force is due to the underlying resilience of the base member and is transmitted through to the patient's dental arch and associated arch structures by means of a teeth engaging member that is also resiliently flexible. If the arch form of the patient is narrow, the appliance generally and particularly the inner and outer frame members thereof, are resilient and can be deformed to be fitted over the underdeveloped arch. The return force then urges the dental arch and associated arch teeth in a direction that would expand the arch form to provide a wider arch in the anterior region of the arch.

Yet further the appliance assists in aligning the dentition on both dental arches. The appliance has upper and lower dental arch receiving channels and it applies a teeth repositioning force that promotes alignment of the teeth along a line defined by the arch receiving channels. The appliance promotes alignment of both protruding and retruding teeth. Further if one or more teeth are rotated, with the distal edge protruding and the mesial edge being retruded, then the inner and outer flanges of the teeth engaging member defining the arch receiving channels apply a force to the protruding or retruded teeth to encourage rotational realignment to the correct position.

The flange or continuous wall on the outer curved frame member of the base member together with the teeth engaging member in particular assists with encouraging alignment of teeth along the arch. Further if one or more teeth are rotated, with the distal edge protruding and the mesial edge is retruded, then the inner and outer flanges of the teeth engaging member also apply a force to encourage rotational realignment to the correct position. The adjacent teeth positioning arrangement also assists with rotational realignment of individual teeth.

Thus in addition to promoting expansion of the arch form the appliance also promotes alignment of the dentition of both the upper and lower dental arches in a row corresponding to the shape of the channels within which the dentition is received. Thus the appliance promotes both arch widening and alignment in a single appliance that is a removable appliance. Applicant believes that this functionality has not previously been obtained in a single orthodontic appliance.

The appliance also has an adjacent teeth positioning arrangement that can also assist in encouraging an arch form to expand over and above the arch expansion promoted by the return force of the appliance when it is deformed. The teeth positioning arrangement can also assist with rotational realignment of individual teeth.

A further advantage of the orthodontic appliance described above is that the silicone rubber is a soft material that has a significant ability to deform. It therefore has the ability to deform significantly to fit the appliance to the dental arch structure of a patient having a shape that is quite different to that of the appliance.

Further the silicone rubber has an ability to cushion the force that is applied by the appliance to the dental arch and dental structures of a patient. As a result the teeth engaging member does not apply excessive local pressure to the teeth and gums, and is comfortable to wear even when the base member has been significantly deformed. This is important when one considers that it is necessary to obtain a certain level of patient comfort when wearing the appliance. For example the patient has to be able to sleep while they are wearing the appliance and also be able to perform other activities when they wear the appliance while they are awake. Further patient compliance is a crucial factor in achieving a successful treatment outcome and wearer comfort is important to achieve this. Further the appliance does not have sharp surfaces that would tend to injure the soft tissues in a patient's mouth.

Another advantage of the appliance described above with reference to the drawings is that it incorporates certain other features that have been shown to improve the myofunctional environment in the patient's mouth by improving on their oral habits. These myofunctional features include a tongue tab for correctly positioning the tongue of the patient. They also include features for inhibiting mouth breathing, incorrect swallowing and tongue thrusting. These features also correctly position the upper jaw relative to the lower jaw whereby to support the TMJ joint.

A yet further advantage is that the orthodontic appliance can be manufactured in a commercial scale manufacturing operation in large quantities. In particular the appliance can be injection moulded in a two step moulding operation in a number of sizes as has been described above in the detailed description which enables it to be produced at reasonable cost. The appliance can be manufactured on a large scale and be supplied to the market at a lower cost than existing orthodontic treatments including braces. This opens up the possibility of orthodontic treatment becoming accessible to a far greater percentage of the global population than is currently the case, particularly in developing countries.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. An orthodontic appliance for developing a developed dental arch form in a patient who has an underdeveloped dental arch form, the appliance comprising a front region that merges with two opposing arm regions that project away from either side of the front region and includes:

an arch-shaped base member that is constructed from a resilient, flexible material, comprising an open frame structure extending substantially in a plane including an arch-shaped outer frame member and an arch-shaped inner frame member that are spaced apart from each other, and a plurality of spaced apart transverse frame members connecting the outer frame member and the inner frame member; and a deformable teeth engaging member constructed from a resilient, flexible material that is softer than the resilient, flexible material of the base member including an arch-shaped web that encloses at least part of the open frame structure, the web forming upper and lower occlusal bite surfaces, and the teeth engaging member defines with the upper and lower occlusal bite surfaces at least one of an upper or a lower dental arch receiving channel, and the web decreases in transverse width in a direction from the arm regions towards the front region so as to correspond with the decrease in width of the occlusal surfaces of a dental arch so that the inner and outer flanges of the teeth engaging member bear against a patient's dental arch and dental arch structures, wherein the appliance has a resting form in which the base member and the teeth engaging member are in their resting condition, and the appliance can be manipulated from the resting form when fitted to a patient to receive the patient's underdeveloped dental arch form into the at least one dental arch receiving channel deforming the open frame structure in the plane thereof, and the appliance exerts a resting form return force urging the underdeveloped dental arch form to develop into the developed dental arch form.

2. An orthodontic appliance according to claim 1, wherein the teeth engaging member has inner and outer flanges that project transversely away from the upper and lower occlusal bite surfaces of the web, whereby to define both upper and lower dental arch receiving channels within which respective upper and lower dental arches of a patient can be received.

3. An orthodontic appliance according to claim 2, wherein the plane of the open frame structure extends substantially parallel to the upper and lower occlusal bite surfaces of the arch-shaped web, and wherein the appliance applies an outward force that bears against the upper and/or lower dental arches of a user in a direction that is substantially parallel to the plane of the open frame structure, when deformed out of its resting position, whereby to develop the underdeveloped dental arch form.

4. An orthodontic appliance according to claim 2, wherein the upper and lower dental arch receiving channels have a shape corresponding to the developed dental arch form when the appliance is in the resting form.

5. An orthodontic appliance according to claim 1, wherein the open frame structure is at least partially received within the arch-shaped web.

6. An orthodontic appliance according to claim 1, wherein the inner and outer flanges and the upper and lower occlusal bite surfaces of the web are arranged so that upper and lower arches of a patient are received within the upper and lower dental arch receiving channels respectively with a tight fit.

7. An orthodontic appliance according to claim 1, wherein the transverse spacing between the inner and outer frame members decreases in a direction from the arm regions to the front region of the appliance, whereby an outline shape of the base member corresponds substantially with that of the web of the teeth engaging member.

8. An orthodontic appliance according to claim 1, wherein the base member includes a first pair of transverse frame members including one transverse frame member towards one side edge of the front region and a further transverse frame member towards the other side edge of the front region, whereby the left and right transverse frame members are substantially aligned with respective left and right outer incisors of a patient, and a front transverse frame member intermediate the first pair of transverse frame members, so that the front region of the appliance is less flexible than the arm regions, and when the appliance is deformed the front region of the appliance applies a greater return force to the arch of a user than the arm regions.

9. An orthodontic appliance according to claim 8, wherein the one and further transverse frame members of the first pair have a width of 1 to 4 mm, and the front transverse frame member has a width of 8 to 12 mm.

10. An orthodontic appliance according to claim 8, wherein the base member further includes a second pair of transverse frame members comprising a left rear transverse frame member towards a free end of an arm region, and a right rear transverse frame member towards a free end of the other arm region, and wherein the base member further includes a third pair of transverse frame members comprising a left transverse frame member positioned intermediate a left transverse frame member of the first pair and the left rear transverse frame member, and a right transverse frame member positioned intermediate a right transverse frame member of the first pair and the right rear transverse frame member.

11. An orthodontic appliance according to claim 1, wherein the material of the base member is resiliently flexible such that it can be deformed by application of a force but tends to return to its original resting form when the force is removed, and the material of the teeth engaging member is a resiliently elastic material that is selected to form a soft cushion for bearing against a dental arch and dental structures of a patient, and wherein the material of the base member and the material of the teeth engaging member are selected so that they flex in unison with each other and resist being delaminated from each other when the appliance is flexed out of its resting condition.

12. An orthodontic appliance according to claim 1, wherein the base member further includes a teeth row repositioning formation comprising an outer flange that projects away from the outer frame member.

13. An orthodontic appliance according to claim 12, wherein the outer flange projects up above the open frame structure and extends along the central front region of the appliance and across a patient's incisor teeth, and wherein the outer flange also extends along at least part of the left and right arm regions of the appliance across a patient's molar teeth.

14. An orthodontic appliance according to claim 12, wherein the teeth engaging member substantially fully encloses the open frame structure and the outer flange of the base member.

15. An oral appliance that is an orthodontic trainer, comprising:
a base member having a generally U-shaped form having left and right arm regions corresponding to the arch of a patient, the base member is in the form of a flat open frame structure comprising curved inner and outer longitudinal frame members that are interconnected by a plurality of transverse frame members, the base member being made of a polymeric material that is resilient and is capable of some bending when the opposing arm regions are pulled towards and away from each other; and
a continuous teeth engaging member made of a material that is softer than the material of the base member, that can conform to the teeth of the patient and that encloses at least part of the base member, wherein the teeth engaging member comprises a central web having upper and lower occlusal bite surfaces that extend parallel to the plane of the open frame structure, and also inner and outer flanges that project transversely away from the upper occlusal bite surface of the web and define at least one of upper and lower teeth channels within which the associated arch and teeth of the patient can be received, and the web decreases in transverse width in a direction from the arm regions towards the front region so as to correspond with the decrease in width of the occlusal surfaces of a dental arch from a molar region towards an incisor region;
wherein the base member is designed with a wide arch such that when deformed inwardly it urges outwardly due to its resilient biasing force, and when it is fitted to a patient having a narrow arch it promotes expansion of the patient's arch.

16. An oral appliance that is an orthodontic trainer according to claim 15, wherein the inner and outer flanges define with the upper occlusal bite surface an upper channel within which the upper dental arch and associated teeth of the patient are receivable.

17. An oral appliance that is an orthodontic trainer according to claim 16, wherein the inner and outer flanges project transversely away from the lower occlusal bite surface of the web and define with the lower occlusal bite surface a lower channel within which the lower dental arch and associated teeth of a user are receivable.

18. An orthodontic appliance for developing a developed dental arch form in a patient who has an underdeveloped dental arch form, the appliance comprising:
an arch-shaped base member that is constructed from a resilient, flexible material having a shape that corresponds generally to a dental arch form; and
a deformable teeth engaging member that substantially encloses at least part of the base member and that defines at least one of an upper or a lower dental arch receiving channel, the teeth engaging member being constructed of a resilient, flexible material that is more flexible than the resilient, flexible material of the base member;
wherein the appliance comprises a front region that merges with two opposing arm regions that project away from either side of the front region, and the front region is constructed with a greater stiffness than the arm regions, and the appliance has a resting form in which the base member and the teeth engaging member are in their resting condition, and wherein the appliance can be manipulated from the resting form when fitted to a patient to receive the patient's underdeveloped dental arch form in the at least one dental arch receiving channel, and wherein the front region, due to said greater stiffness, exerts a greater resting form return force against the patient's underdeveloped dental arch form than that exerted by the arm regions, urging the underdeveloped dental arch form to develop into the developed dental arch form; and the teeth engaging member includes a web that decreases in transverse width in a direction from the arm regions towards the front region so as to correspond with the decrease in width of the occlusal surfaces of a dental arch, so that the teeth engaging member bears against a patient's dental arch and dental arch structures.

19. A method of treating a patient to encourage development of a dental arch form in a patient who has an underdeveloped arch form, said method including the steps of:

fitting an orthodontic appliance over a dental arch of a patient within the mouth of the patient, said orthodontic appliance including:

an arch-shaped base member that is constructed from a resilient, flexible material, comprising an open frame structure extending substantially in a plane including an arch-shaped outer frame member and an arch-shaped inner frame member that are spaced apart from each other, and a plurality of spaced apart transverse frame members connecting the outer frame member and the inner frame member; and a deformable teeth engaging member including an arch-shaped web that encloses at least part of the open frame structure, the web forming upper and lower occlusal bite surfaces, and the teeth engaging member defining with the upper and lower occlusal bite surfaces at least one of an upper or a lower dental arch receiving channel, the teeth engaging member being constructed from a resilient, flexible material that is softer than the resilient, flexible material of the base member;

wherein the appliance has a resting form in which the base member and the teeth engaging member are in their resting condition, and the appliance can be manipulated from the resting form when fitted to a patient to receive the patient's underdeveloped dental arch form into the at least one dental arch receiving channel deforming the open frame in the plane thereof, and the appliance exerts a resting form return force urging the underdeveloped dental arch form to develop into the developed dental arch form; and having the patient wear the orthodontic appliance on a regular basis whereby to progressively develop the arch form.

20. A method according to claim 19, including developing the upper arch form of a patient having a class 2 malocclusion with an underdeveloped upper arch form in the mid-facial region, and also aligning the dentition of the underdeveloped upper arch form of the patient while developing the upper arch form.

\* \* \* \* \*